(12) United States Patent
Harashima et al.

(10) Patent No.: US 8,981,044 B2
(45) Date of Patent: Mar. 17, 2015

(54) LIPID MEMBRANE STRUCTURE HAVING INTRANUCLEAR MIGRATING PROPERTY

(75) Inventors: Hideyoshi Harashima, Hokkaido (JP); Hidetaka Akita, Hokkaido (JP); Mohammad Shaheen Sharif, Hokkaido (JP); Takashi Nakamura, Hokkaido (JP); Soichiro Ishii, Hokkaido (JP); Shiroh Futaki, Kyoto (JP)

(73) Assignee: National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 13/641,812

(22) PCT Filed: Apr. 20, 2011

(86) PCT No.: PCT/JP2011/059738
§ 371 (c)(1),
(2), (4) Date: Jan. 22, 2013

(87) PCT Pub. No.: WO2011/132713
PCT Pub. Date: Oct. 27, 2011

(65) Prior Publication Data
US 2013/0122054 A1    May 16, 2013

(30) Foreign Application Priority Data
Apr. 21, 2010    (JP) .................................. 2010-097888

(51) Int. Cl.
| | | |
|---|---|---|
| C07K 14/00 | (2006.01) | |
| A61K 47/42 | (2006.01) | |
| A61K 9/127 | (2006.01) | |
| A61K 31/711 | (2006.01) | |
| A61K 39/39 | (2006.01) | |
| A61K 47/48 | (2006.01) | |
| A61K 48/00 | (2006.01) | |
| C12N 15/00 | (2006.01) | |
| C12N 15/88 | (2006.01) | |
| A61K 39/00 | (2006.01) | |

(52) U.S. Cl.
CPC ............... *A61K 47/42* (2013.01); *A61K 9/127* (2013.01); *A61K 9/1272* (2013.01); *A61K 31/711* (2013.01); *A61K 39/39* (2013.01); *A61K 47/48* (2013.01); *A61K 47/48238* (2013.01); *A61K 47/48815* (2013.01); *A61K 48/0041* (2013.01); *C12N 15/00* (2013.01); *C12N 15/88* (2013.01); *A61K 2039/55555* (2013.01); *A61K 2039/5154* (2013.01); *C12N 2810/40* (2013.01)
USPC .......................................... 530/300; 530/324

(58) Field of Classification Search
None
See application file for complete search history.

(56) References Cited

U.S. PATENT DOCUMENTS

| | | |
|---|---|---|
| 2002/0055174 A1 | 5/2002 | Rittner et al. |
| 2003/0203865 A1 | 10/2003 | Harvie et al. |
| 2005/0025821 A1 | 2/2005 | Harvie et al. |
| 2005/0147993 A1 | 7/2005 | Khan |
| 2006/0058254 A1 | 3/2006 | Dina et al. |
| 2006/0211647 A1 | 9/2006 | Khan |
| 2007/0059353 A1 | 3/2007 | Harashima et al. |
| 2007/0299244 A1 | 12/2007 | Chaki et al. |
| 2008/0222750 A1 | 9/2008 | Khan |
| 2009/0047272 A1 | 2/2009 | Appelbaum et al. |
| 2009/0123468 A1 | 5/2009 | Khan |
| 2009/0305409 A1 | 12/2009 | Kogure et al. |
| 2010/0104623 A1 | 4/2010 | Harashima et al. |

FOREIGN PATENT DOCUMENTS

| | | |
|---|---|---|
| CN | 1863558 | 11/2006 |
| EP | 1 161 957 | 12/2001 |
| EP | 1 867 726 | 12/2007 |
| EP | 2 138 192 | 12/2009 |
| JP | 2002-316997 | 10/2002 |
| JP | 2006-28030 | 2/2006 |
| JP | 2007-508846 | 4/2007 |
| WO | 02/088318 | 11/2002 |
| WO | 2004/058179 | 7/2004 |
| WO | 2005/032593 | 4/2005 |
| WO | 2005/115444 | 12/2005 |
| WO | WO 2005115444 A2 * | 12/2005 |
| WO | 2006/101201 | 9/2006 |
| WO | 2007/102481 | 9/2007 |
| WO | 2008/105178 | 9/2008 |
| WO | 2010/011890 | 1/2010 |

OTHER PUBLICATIONS

Harding, Clifford V. et al; "Liposome encapsulated antigens engender lysosomal processing for class II mhc presentation and cytosolic processing for class I presentation." J. Immunol., (1991) 147(9) p. 2860-2863.*

Caron, Nicholas J. et al; "Endosome disruption enhances the functional nuclear delivery of tat-fusion proteins." Biochem. and Biophys. Res. Comm. (2004) 319 p. 12-20.*

Lee, Haeshin et al; "PEG grafted plylysine with fusogenic peptide for gene delivery: high transfection efficiency with low cytotoxicity." J. Cont. Rel. (2002) 79 p. 283-291.*

Park, Jinseu et al; "Mutational analysis of a human immunodeficiency virus type 1 tat protein transduction domain which is required for deliery of an exogenous protein into mammalian cells." J. Gen. Virol. (2002) 83 p. 1173-1181.*

(Continued)

*Primary Examiner* — Maury Audet
*Assistant Examiner* — Fred Reynolds
(74) *Attorney, Agent, or Firm* — Greenblum & Bernstein, P.L.C.

(57) ABSTRACT

A lipid membrane structure for delivering a substance into a nucleus of a cell, wherein lipid membrane is modified with (a) a polypeptide comprising the amino acid sequence of SEQ ID NO: 1, and/or (b) a polypeptide consisting of an amino acid sequence comprising the amino acid sequence of SEQ ID NO: 1, but including deletion and/or substitution and/or insertion of one or several amino acid residues, and having an activity of promoting migration of the lipid membrane structure into a nucleus of a cell, which can efficiently deliver a nucleic acid into a nucleus of an immunocyte such as dendritic cell.

10 Claims, 8 Drawing Sheets

(56) References Cited

OTHER PUBLICATIONS

Torchilin, Vladimir P. et al; "Cell transfection in vitro and in vivo with noontoxic tat peptide liposome dna complexes." PNAS (2003) 100(4) p. 1972-1977.*

Jorgensen, Helle F. et al; "Mbd1 is recruited to both methylated and nonmethylated cpgs via distinct dna binding domains." Mol. Cell Biol. (2004) 24(8) p. 3387-3395.*

Torchillin, Vladimir P. et al; "Cell transfection in vitro and in vivo with nontoxic tat peptide liposome dna complexes." PNAS (2003) 100(4) p. 1972-1977.*

Falk, Kirsten et al; "Allele specific motifs revealed by sequencing of self-peptides eluted from mhc molecules." Nature (1991) 351 p. 290-296.*

Gershon, Hezi et al, "Mode of formation and structural features of dna-cationic liposome complexes used for transfection." Biochemistry (1993) 32 p. 7143-7151.*

Vlasov, G. P. et al, "Optimization of transfectionproperties of dna-lysine dendrimer complexes." Russ. J. Bioorg. Chem. (2005) 31(2) p. 153-159.*

Mihara, Hisakazu et al, "Design and synthesis of amphiphilic basic peptides with antibacterial activity and their interaction with model membrane." J. Chem. Soc. Japan (1987) 60(2) p. 697-706.*

S.H. Min et al., "A composite gene delivery system consisting of polyethylenimine and an amphipathic peptide KALA", J. Gene Med. vol. 8, No. 12, 2006, pp. 1425-1434.

Tomoyuki Kakudo et al., "Controlled Intracellular Trafficking Using Plasma and Endosomal Membreane Interactive Peptides", Membrane 28(2), 2003, pp. 46-54.

Sharif Mohammad Shaheen et al., "MHC Class-I mediated antigen presentation by KALA modified T-MEND vector expressing a high luciferase activity in murine derived dendritic cells (JAWS-II)", Drug Deliverly System 25(3), May 2010, pp. 310.

Search report from International Application No. PCT/JP2011/059738, mail date is May 24, 2011.

International Preliminary Report on Patentability and Written Opinion of the Searching Authority for International Application No. PCT/JP2011/059738, mail date is Nov. 14, 2012.

Akita et al. "Development of multifunctional envelope-type nano-device (MEND) based on the regulation of intracellular trafficking," Drug Delivery System, 22-2, 2007, pp. 115-122.

Subbarao et al. "pH-Dependent Bilayer Destabalization by an Amphipathic Peptide," Biochemistry, vol. 26, No. 11, 1987, pp. 2964-2972.

Kakudo et al., "Transerrin-Modified Liposomes Equipped with a pH-Sensitive Fusogenic Peptide: An Artificial Viral-like Delivery System," Biochemistry, vol. 43, No. 19, 2004, pp. 5618-5623.

Kogure et al., "Development of a non-viral multifunctional envelope-type nano device by a novel lipid film hydration method," Journal of Controlled Release, 98, 2004, pp. 317-323.

Wyman et al., "Design, Synthesis, and Characterization of a Cationic Peptide That Binds to Nucleic Acids and Permeabilizes Bilayers," Biochemistry, vol. 36, No. 10, 1997, pp. 3008-3017.

U.S. Appl. No. 13/642,699 to Hideyoshi Harashima et al., filed Oct. 22, 2013.

Hatakayama et al. "Development of a novel systemic gene delivery system for cancer therapy with a tumor-specific cleavable PEG-lipid" *Gene Therapy* 14:68-77, published online Aug. 17, 2006.

Office Action issued with respect to Chinese Patent Application No. 201180019916 6, mailed Dec. 2, 2013, along with a partial English language translation.

Extended European Search Report issued with respect to European Patent Application No. 11772046 6, mailed Jan. 24, 2014.

Shoko Kobayashi et al., "Tanpakushitsu no Kakusotatsu o Mezashita Cation-sei Shishitsu/pH Kanjusei Peptide-kei no Riyo", Abstracts of Annual Meeting of Pharmaceutical Society of Japan, vol. 128th, No. 3, 2008, pp. 22.

Hidetaka Akita et al., "Dai 4 Sho Idenshi Donyu no Tameno Saibo Seibutsu Igaku to sono Kanren Gijutsu, 8. Saibo-nai Traffic", Gene & Medicine Mook, No. 5, 2006, pp. 228-234.

Hyejung Mok et al., "Self-Crosslinked and Reducible Fusogenic Peptides for Intracellular Delivery of siRNA", Biopolymers, vol. 89, No. 10, 2008, pp. 881-888.

Andrew Miller, "Cationic Liposomes for Gene Therapy", Angew. Chem. Int. Ed., vol. 37, 1998, pp. 1768-1785.

Office Action for Chinese Patent Application No. 201180019916.6, dated Oct. 27, 2014, along with an English language translation.

* cited by examiner

Days after tumor transplantation

LIPID MEMBRANE STRUCTURE HAVING INTRANUCLEAR MIGRATING PROPERTY

SEQUENCE LISTING

The instant application contains a Sequence Listing which has been submitted in ASCII format via EFS-Web and is hereby incorporated by reference in its entirety. Said ASCII copy, created on Jul. 15, 2014 is named P42676 SL.txt and is 5,643 bytes in size.

TECHNICAL FIELD

The present invention relates to a lipid membrane structure having intranuclear migrating property. More specifically, the present invention relates to a lipid membrane structure such as liposome that can easily migrate into the nucleus of an immunocyte, especially the nucleus of dendritic cell.

BACKGROUND ART

As a means for transporting a medicament specifically to a pathological lesion, methods of encapsulating a medicament in liposomes have been proposed. In particular, in the field of therapeutic treatments of malignant tumors, many reports have been made as for effectiveness of liposomes encapsulating an antitumor agent. Further, a multifunctional envelope-type nano device (MEND: henceforth sometimes abbreviated as "MEND" in the specification, see, for example, Drug Delivery System, 22-2, pp. 115-122, 2007 and the like) has been proposed. This structure can be used as a drug delivery system for delivering a gene or the like selectively into particular cells, and is known to be useful for, for example, gene therapy of tumors and the like.

Variety of methods have been proposed for modifying the surface of a lipid membrane structure with a functional molecule, as means for delivering an objective substance such as medicaments, nucleic acids, peptides, polypeptides, and saccharides to specific parts such as target organs and tumor tissues using a lipid membrane structure. When a lipid membrane structure encapsulating a medicament such as antitumor agent reaches a target cell, the structure is taken up into the cell by endocytosis and enclosed in the endosome. Then, the structure releases the encapsulated medicament into the cytoplasm due to hydrolytic action of an enzyme in the lysosome or the like. In order to enhance the release of medicament from a liposome taken up into the endosome, a liposome has been proposed of which surface is modified with a peptide, GALA (Biochemistry, 26, pp.2964-2972, 1987 for the peptide (SEQ ID NO: 13); Biochemistry, 43, pp.5618-5623, 2004 for the liposome) and MEND (Japanese Patent Unexamined Publication (KOKAI) No. 2006-28030).

Further, as means for localization of a lipid membrane structure encapsulating an objective substance such as nucleic acid into the nucleus of a target cell, there have been proposed, for example, a liposome of which outer surface is modified with octaarginine (SEQ ID NO: 4) (International Patent Publication WO2005/32593; Journal of Controlled Release, 98, pp.317-323, 2004), a bilamellar liposome having a lipid membrane modified with a nucleus permeable peptide (International Patent Publication WO2006/101201), and a liposome of which surface is modified with a monosaccharide such as galactose and mannose (International Patent Publication WO2007/102481). It has been reported that a multilamellar lipid membrane structure (T-MEND) modified with a monosaccharide has fusability with a lipid membrane and a nuclear membrane, and is capable of improving gene expression efficiency as an experimental result in vitro.

If a nucleic acid encoding an antigenic protein can be introduced into the nucleus of an immunocyte, especially dendritic cell having an antigen-presenting action, a protein transcribed and translated from the nucleic acid in the dendritic cell can be presented as an antigen on the surface of the dendritic cell, and the host organism can acquire immunity against that protein. From such point of view, a technique for efficiently delivering a nucleic acid into the nucleus of immunocyte, such as dendritic cell has been desired.

However, where a nucleic acid is introduced into the nucleus of dendritic cell by using a lipid membrane structure such as the aforementioned MEND, the nucleic acid introduction efficiency is insufficient compared with introduction into other cells, for example, tumor cells and hepatic parenchymal cells. Before an introduced nucleic acid is finally expressed in the nucleus, the nucleic acid inevitably undergoes various intracellular kinetic processes such as uptake into cell, escape from endosome, migration into nucleus, and intranuclear transcription. However, in nondividing cells such as dendritic cell, an intact double-layered nuclear membrane constantly exist, and it is estimated that this nuclear membrane inhibits the intranuclear migrating ability of the lipid membrane structure. Therefore, in order to deliver a nucleic acid into the nucleus of dendritic cell by using a lipid membrane structure, it is a very important object how the nucleic acid successfully overcomes each of the aforementioned processes, especially, the barrier of the double-layered nuclear membrane.

In addition, a polypeptide consisting of 30 amino acid residues called KALA peptide (SEQ ID NO: 5) is known, and it has been reported that the peptide can form a complex with a plasmid DNA using cationic charge of itself (Biochemistry, 36, pp.3008-3017, 1997). However, this reference fails to suggest whether or not this peptide promotes intranuclear migration of a lipid membrane structure.

PRIOR ART REFERENCES

Patent documents

Patent document 1: International Patent Publication WO2005/32593
Patent document 2: International Patent Publication WO2006/101201
Patent document 3: International Patent Publication WO2007/102481
Patent document 4: Japanese Patent Unexamined Publication (KOKAI) No. 2006-28030

Non-Patent Documents

Non-patent document 1: Drug Delivery System, 22-2, pp. 115-122, 2007
Non-patent document 2: Biochemistry, 26, pp. 2964-2972, 1987
Non-patent document 3: Biochemistry, 43, pp. 5618-5623, 2004
Non-patent document 4: Journal of Controlled Release, 98, pp. 317-323, 2004
Non-patent document 5: Biochemistry, 36, pp. 3008-3017, 1997

SUMMARY OF THE INVENTION

Object to be Achieved by the Invention

An object of the present invention is to provide a means for efficiently delivering a nucleic acid into the nucleus of an immunocyte, especially dendritic cell having an antigen-presenting ability. More specifically, the object of the present invention is to provide a lipid membrane structure that can efficiently deliver a nucleic acid into the nucleus of an immunocyte such as dendritic cell.

Means for Achieving the Object

In order to achieve the aforementioned object, the inventors of the present invention attempted to introduce a nucleic acid enclosed in MEND modified with an octaarginine polypeptide (SEQ ID NO: 4) as a functional polypeptide that can enhance nuclear migrating property (International Patent Publication WO2005/32593), or MEND modified with the GALA peptide (SEQ ID NO: 13) as a functional polypeptide that imparts endosomal escaping ability (Japanese Patent Unexamined Publication (KOKAI) No. 2006-28030) into dendritic cells, but almost no expression of a polypeptide from the nucleic acid was observed. Further, they also attempted to introduce a nucleic acid encapsulated in a multilamllar lipid membrane structure (T-MEND) comprising a lipid membrane having fusability with the endosome and a lipid membrane having fusability with the nuclear membrane into dendritic cells. However, presentation of a polypeptide expressed from the introduced nucleic acid on the surfaces of the dendritic cells was not observed, although promotion of the expression of the polypeptide was slightly observed in the nucleus.

In order to achieve the aforementioned object, the inventors of the present invention attempted to introduce a nucleic acid enclosed in MEND modified with an octaarginine polypeptide as a functional polypeptide that can enhance nuclear migrating property (International Patent Publication WO2005/32593), or MEND modified with the GALA peptide as a functional polypeptide that imparts endosomal escaping ability (Japanese Patent Unexamined Publication (KOKAD No. 2006-28030) into dendritic cells, but almost no expression of a polypeptide from the nucleic acid was observed. Further, they also attempted to introduce a nucleic acid encapsulated in a multilamllar lipid membrane structure (T-MEND) comprising a lipid membrane having fusability with the endosome and a lipid membrane having fusability with the nuclear membrane into dendritic cells. However, presentation of a polypeptide expressed from the introduced nucleic acid on the surfaces of the dendritic cells was not observed, although promotion of the expression of the polypeptide was slightly observed in the nucleus.

The inventors of the present invention further conducted researches, and as a result, found that when a lipid membrane of a lipid membrane structure such as MEND encapsulating a nucleic acid was modified with KALA peptide, efficiency of nucleic acid introduction into the nuclei of immunocytes such as dendritic cells was remarkably increased. The present invention was accomplished on the basis of the aforementioned finding.

The present invention thus provides a lipid membrane structure for delivering a substance into a nucleus of a cell, wherein lipid membrane is modified with the following polypeptide (a) and/or polypeptide (b):
(a) a polypeptide consisting of the amino acid sequence of SEQ ID NO: 1;
(b) a polypeptide consisting of an amino acid sequence including deletion and/or substitution and/or insertion of one or several amino acid residues in the amino acid sequence of SEQ ID NO: 1, which polypeptide has an activity of promoting migration of the lipid membrane structure into a nucleus of a cell.

According to preferred embodiments of the aforementioned lipid membrane structure, there are provided the aforementioned lipid membrane structure, wherein the lipid membrane structure is a liposome; the aforementioned lipid membrane structure, wherein the cell is an immunocyte, preferably dendritic cell; the aforementioned lipid membrane structure, wherein the polypeptides (a) and/or (b) are modified with a hydrophobic group, preferably stearyl group, cholesteryl group, or the like, and the hydrophobic group is inserted into the lipid membrane; the aforementioned lipid membrane structure, which has a polypeptide containing a plurality of contiguous arginine residues, preferably a polypeptide containing 4 to 20 contiguous arginine residues (SEQ ID NO: 3), more preferably a polypeptide consisting only of 4 to 20 contiguous arginine residues (SEO ID NO: 3), most preferably octaarginine (SEO ID NO: 4), on the surface thereof; the aforementioned lipid membrane structure, which has a polyalkylene glycol or a polyalkylene glycol, preferably a polyethylene glycol (PEG), condensed with a phospholipids, on the surface thereof; and the aforementioned lipid membrane structure, wherein ratio of cationic lipids to the total lipids constituting a lipid bilayer is 0 to 40% (molar ratio).

Further, as another embodiment, there is provided any of the aforementioned lipid membrane structures, wherein a substance to be delivered is encapsulated in the inside of the lipid membrane structure. According to preferred embodiments of this invention, there are provided any of the aforementioned lipid membrane structures, wherein the substance to be delivered is a nucleic acid, for example, a functional nucleic acid such as a nucleic acid containing a gene or an siRNA; the aforementioned lipid membrane structure, wherein the substance to be delivered is DNA; the aforementioned lipid membrane structure, wherein the DNA is a DNA ligated with a vector DNA that does not contain CpG; the aforementioned lipid membrane structure, wherein the DNA does not contain CpG, and the DNA is a DNA ligated with a vector DNA that does not contain CpG; the aforementioned lipid membrane structure, wherein the substance to be delivered is a nucleic acid encoding an antigen polypeptide to be presented on the surface of an immunocyte, preferably surface of dendritic cell; any of the aforementioned lipid membrane structures, wherein the lipid membrane structure is a multifunctional envelope-type nano device (MEND); and any of the aforementioned lipid membrane structures, wherein a nucleic acid and a cationic polymer, preferably protamine, are encapsulated in the inside of the lipid membrane structure.

There are also provided the aforementioned lipid membrane structure, which is used for introducing a nucleic acid encoding an antigen polypeptide to be presented on the surface of an immunocyte, preferably surface of dendritic cell, into a nucleus of the immunocyte; the aforementioned lipid membrane structure, which is for use in immunotherapy against the aforementioned antigen polypeptide; and the aforementioned lipid membrane structure, wherein the antigen polypeptide is a surface polypeptide specific to a cancer cell. The present invention also provides a pharmaceutical composition containing the above lipid membrane structure as an active ingredient, preferably a pharmaceutical composition containing a nucleic acid as a substance to be delivered.

As other aspects of the present invention, there are provided a method for delivering a nucleic acid into a nucleus of a cell, preferably a nucleus of an immunocyte, more preferably a nucleus of dendritic cell, of a mammal including human in vivo, which comprises the step of administering, to the mammal, the aforementioned lipid membrane structure encapsulating the nucleic acid inside thereof; and a method for presenting an antigen polypeptide on the surface of an immunocyte, preferably dendritic cell, in a mammal including human in vivo, which comprises the step of administering, to the mammal, the aforementioned lipid membrane structure encapsulating a nucleic acid encoding the antigen polypeptide inside thereof.

There are also provided a method for presenting in vivo an antigen polypeptide on the surface of an immunocyte, preferably dendritic cell, in a mammal including human for immunization against the antigen polypeptide, which comprises the step of administering, to the mammal, the aforementioned lipid membrane structure encapsulating a nucleic acid encoding the antigen polypeptide inside thereof and a method for immunotherapy of a malignant tumor by presenting in vivo a surface polypeptide specific to a cancer cell on the surface of an immunocyte, preferably dendritic cell, in a mammal including human for immunization against the polypeptide, which comprises the step of administering, to the mammal, the aforementioned lipid membrane structure encapsulating a nucleic acid encoding the polypeptide inside thereof.

The present invention further provide a polypeptide used for promoting migration of a lipid membrane structure into a nucleus of a cell, preferably a nucleus of an immunocyte, more preferably a nucleus of dendritic cell, which consists of the following polypeptide (a) and/or polypeptide (b):
(a) a polypeptide consisting of the amino acid sequence of SEQ ID NO: 1;
(b) a polypeptide consisting of an amino acid sequence including deletion and/or substitution and/or insertion of one or several amino acid residues in the amino acid sequence of SEQ ID NO: 1.

Effect of the Invention

The lipid membrane structure provided by the present invention can efficiently migrate into a nucleus of an arbitrary cell, such as immunocytes including dendritic cell, and can effectively release an encapsulated substance such as nucleic acid in the nucleus to induce expression of a polypeptide encoded by the nucleic acid. Where a nucleic acid encoding a polypeptide is introduced into the nucleus of dendritic cell by using the lipid membrane structure of the present invention, the polypeptide transcribed and translated from the nucleic acid is presented on the surface of the dendritic cell, and the living host can acquire immunity against the polypeptide. Therefore, it becomes possible to perform effective immunotherapy against any desired polypeptides.

Further, the lipid membrane structure provided by the present invention also has a characteristic feature that the lipid membrane structure itself can exhibit an adjuvant action for dendritic cells and promote production of various cytokines. Therefore, by administering dendritic cells transformed with the lipid membrane structure provided by the present invention, exacerbation or proliferation of tumor can be remarkably suppressed irrespective of the presence or absence of an adjuvant, and by administering the lipid membrane structure encapsulating an antigen protein, cytotoxicity can be enhanced in vivo. Furthermore, the lipid membrane structure also has a characteristic feature that, where CpG sequence is eliminated if desired from the vector moiety of DNA to be encapsulated, and also from DNA encoding a protein to be expressed, gene expression efficiency is markedly improved.

BRIEF DESCRIPTION OF THE DRAWINGS

FIG. 6 discloses SEQ ID NOS 6-7, respectively, in order of appearance.

FIG. 7 discloses SEQ ID NOS 7-8, respectively, in order of appearance.

FIG. 8 discloses SEQ ID NOS 9-12, respectively, in order of appearance.

MODES FOR CARRYING OUT THE INVENTION

Figure 1:
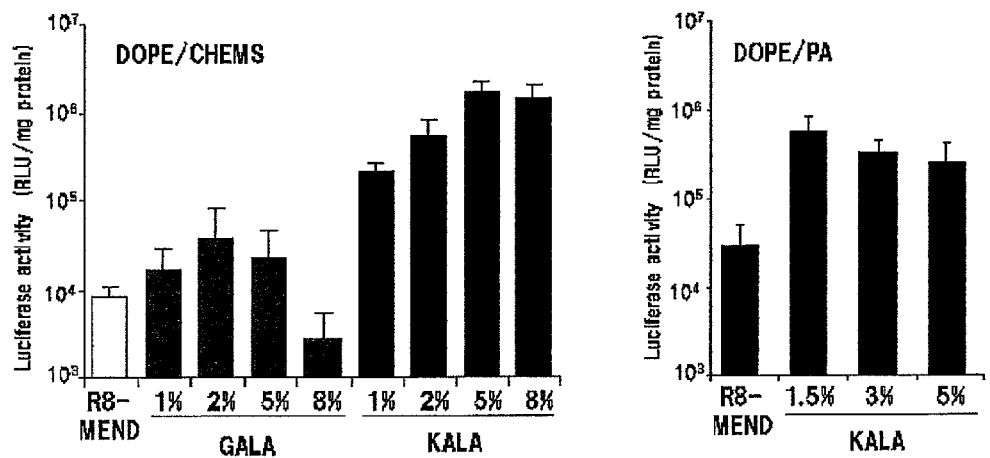
[FIG. 1] This figure depicts expression efficiency obtained with MEND of which lipid membrane was modified with the polypeptide (a) (KALA) (SEQ ID NO: 1) or with the polypeptide GALA (SEQ ID NO: 13) or with the polypeptide R8 (SEQ ID NO: 4).

Examples of lipids constituting the lipid membrane structure of the present invention include, for example, phospholipids, glycolipids, sterols, saturated or unsaturated fatty acids, and the like.

Examples of the phospholipids and phospholipid derivatives include, for example, phosphatidylethanolamine, phosphatidylcholine, phosphatidylserine, phosphatidylinositol, phosphatidylglycerol, cardiolipin, sphingomyelin, ceramide phosphorylethanolamine, ceramide phosphorylglycerol, ceramide phosphorylglycerol phosphate, 1,2-dimyristoyl-1, 2-deoxyphosphatidylcholine, plasmalogen, phosphatidic acid, and the like, and one or more kinds of these can used independently or in combination. Although the fatty acid residues of these phospholipids are not particularly limited, examples include saturated or unsaturated aliphatic acid residues having 12 to 20 carbon atoms, and specific examples include, for example, acyl groups derived from such a fatty acid as lauric acid, myristic acid, palmitic acid, stearic acid, oleic acid, and linoleic acid. Further, a phospholipid derived from a natural product such as egg yolk lecithin and soybean lecithin can also be used.

Examples of the glycolipids include glyceroglycolipids (for example, sulfoxyribosyl glyceride, diglycosyl diglyceride, digalactosyl diglyceride, galactosyl diglyceride, and glycosyl diglyceride), sphingoglycolipids (for example, galactosyl cerebroside, lactosyl cerebroside and ganglioside), and the like.

Examples of the sterols include animal-derived sterols (for example, cholesterol, cholesterol succinate, lanosterol, dihydrolanosterol, desmosterol and dihydrocholesterol), plant-derived sterols (phytosterol) (for example, stigmasterol, sitosterol, campesterol and brassicasterol), microorganism-derived sterols (for example, thymosterol and ergosterol), and the like.

Examples of the saturated or unsaturated fatty acids include saturated or unsaturated fatty acids having 12 to 20 carbon atoms, such as palmitic acid, oleic acid, stearic acid, arachidonic acid, and myristic acid.

Form of the lipid membrane structure is not particularly limited, and examples of the form in which lipid membrane structures are dispersed in an aqueous solvent include unilamella liposomes, multi-lamella liposomes, O/W type emulsions, W/O/W type emulsions, spherical micelles, fibrous micelles, layered structures of irregular shapes and the like. Examples of preferred form of the lipid membrane structure of the present invention include liposomes. Although liposomes may be explained hereafter as a preferred embodiment of the lipid membrane structure of the present invention, the lipid membrane structure of the present invention is not limited to liposomes.

The lipid membrane structure of the present invention is used for delivering a substance into a nucleus of a cell, and is characterized in that the lipid membrane is modified with the following polypeptide (a) and/or polypeptide (b): (a) a polypeptide consisting of the amino acid sequence of SEQ ID NO: 1; and (b) a polypeptide consisting of an amino acid sequence including deletion and/or substitution and/or insertion of one or several amino acid residues in the amino acid sequence of SEQ ID NO: 1, which polypeptide has an activity of promoting migration of the lipid membrane structure into a nucleus of a cell.

The aforementioned polypeptide (a) represented by SEQ ID NO: 1 is a polypeptide consisting of 27 amino acid residues obtained by eliminating three amino acid residues from the C-terminus of the known polypeptide (WEAK-LAKALAKALAKHLAKALAKALKACEA (SEQ ID NO: 5)) consisting of 30 amino acid residues (henceforth this polypeptide may be called "KALA peptide" in this specification, Biochemistry, 36, pp.3008-3017, 1997). Although this reference describes that the polypeptide can form a complex with a plasmid DNA using cationic charge of itself, the reference fails to describe whether or not this peptide promotes intranuclear migration of a lipid membrane structure. Further, the known KALA peptide (SEQ ID NO: 5) comprises the sequence of the functional polypeptide consisting of 30 amino acid residues called GALA peptide (SEQ ID NO: 13) (Biochemistry, 26, pp. 2964-2972, 1987) including substitution of a plurality of amino acid residues with other amino acid residues (for example, a plurality of glutamine residues are replaced by lysine residues). However, the GALA peptide (SEQ ID NO: 13) has a function of promoting fusion of lipid membranes in response to pH, and a function of enhancing ability of a lipid membrane structure to escape from the endosome, and these functions are different from the function of the KALA peptide used in the present invention (function of improving intranuclear migrating property of a lipid membrane structure in a cell).

In the present invention, the polypeptide (b): a polypeptide consisting of an amino acid sequence including deletion and/or substitution and/or insertion of one or several amino acid residues in the amino acid sequence of SEQ ID NO: 1 (henceforth referred to as "modified polypeptide"), and having an activity of promoting migration of the lipid membrane structure into a nucleus of a cell may also be used. As the activity of promoting migration of the lipid membrane structure into the nucleus, for example, activity of promoting ability to migrate into the nucleus of dendritic cell can be evaluated. Where dendritic cell is as the target cell and the lipid membrane structures is used which encapsulates a nucleic acid inside thereof in a state that the nucleic acid can be expressed in the nucleus of the cell, for example, a nucleic acid encoding a polypeptide that is ligated downstream with a promoter operable in the nucleus of dendritic cell, the evaluation can be performed, for example, by preparing a lipid membrane structure wherein lipid membrane thereof is modified with the modified polypeptide (henceforth this lipid membrane structure is referred to as "modified lipid membrane structure"), and also by preparing a lipid membrane structure in which lipid membrane is not modified with the modified polypeptide (henceforth this lipid membrane structure is referred to as "unmodified lipid membrane structure"), and determining whether or not expression amount of the marker peptide in a cell introduced with the modified lipid membrane structure is increased compared with that of the marker peptide in a cell introduced with the unmodified lipid membrane structure. When an increase in the expression amount is observed, tha modified polypeptide can be used as the aforementioned polypeptide (b). It is also possible to use one or more kinds of the aforementioned polypeptide (b) in combination with the polypeptide (a).

The aforementioned polypeptide (a) and polypeptide (b) can be biologically prepared by using a host cell with various kinds of gene recombination techniques available to those skilled in the art. The aforementioned polypeptides may also be prepared by an organic chemical method utilizing a peptide synthesis reaction available for those skilled in the art, such as the solid phase synthesis method. Alternatively, they may also be automatically synthesized by using a peptide synthesizer.

Although a means for fixing the aforementioned polypeptide (a) and/or polypeptide (b) to the lipid membrane of the lipid membrane structure is not particularly limited, the modification of the lipid membrane can be easily attained by, for example, modifying the aforementioned polypeptide (a) and/or polypeptide (b) with a hydrophobic group such as stearyl group or cholesteryl group, and preparing the lipid membrane structure so that the hydrophobic group is buried in the lipid membrane of the lipid membrane structure. As the hydrophobic group, a residue of arbitrary hydrophobic compound can be used. When a liposome having a multilamellar lipid membrane is used as the lipid membrane structure, the modification of lipid membrane with the aforementioned polypeptide (a) and/or polypeptide (b) may be performed for an inner lipid membrane as well as for an outer lipid membrane.

The lipid membrane structure of the present invention can be used for delivering a substance into a nucleus of a cell. Type of the cell is not particularly limited, and an arbitrary cell can be used as the target depending on a type of the substance to be delivered, purpose of the delivery of substance into the nucleus, and the like. Preferred examples of the cell to be the target include immunocytes, and among immunocytes, antigen-presenting cells are preferably used. For example, antigen-presenting cells such as macrophage, dendritic cell, and B cell are preferred, and dendritic cell is particularly preferred.

In order to promote permeation of the lipid membrane structure of the present invention into nuclei, surface of the lipid membrane structure can also be modified with, for example, a tri- or higher oligosaccharide compound. Although type of the tri- or higher oligosaccharide compound is not particularly limited, for example, an oligosaccharide compound comprising about 3 to 10 of linked saccharide units can be used, and an oligosaccharide compound comprising about 3 to 6 of linked saccharide units can be preferably used.

More specifically, examples of the oligosaccharide compound include, for example, trisaccharide compounds such as cellotriose (β-D-glucopyranosyl-(1->4)-β-D-glucopyranosyl-(1->4)-D-glucose), chacotriose (α-L-rhamnopyranosyl-(1->2)-[α-L-rhamnopyranosyl-(1->4)]-D-glucose), gentianose (β-D-fructofuranosyl-β-D-glucopyranosyl-(1->6)-α-D-glucopyranoside), isomaltotriose (α-D-glucopyranosyl-(1->6)-α-D-glucopyranosyl-(1->6)-D-glucose), isopanose (α-D-glucopyranosyl-(1->4)-α-D-glucopyranosyl-(1->4)-D-glucose), maltotriose (α-D-glucopyranosyl-(1->4)-α-D-glucopyranosyl-(1->4)-D-glucose), manninotriose (α-D-galactopyranosyl-(1->6)-α-D-galactopyranosyl-(1->6)-D-glucose), melezitose (α-D-glucopyranosyl-(1->3)-β-D-fructofuranosyl=α-D-glucopyranoside), panose (α-D-glucopyranosyl-(1->6)-α-D-glucopyranosyl-(1->4)-D-glucose), planteose (α-D-galactopyranosyl-(1->6)-β-D-fructofuranosyl=α-D-glucopyranoside), raffinose (β-D-fructofuranosyl=α-D-galactopyranosyl-(1->6)-α-D-glucopyranoside), solatriose (α-L-rhamnopyranosyl-(1->2)-[β-D-glucopyranosyl-(1->3)]- D-galactose), and umbelliferose (β-D-fructofuranosyl=α-D-galactopyranosyl-(1->2)-α-D-galactopyranoside; tetrasaccharide compounds such as lycotetraose (β-D-glucopyranosyl-(1->2)-[β-D-xylopyranosyl-(1->3)]-β-D-glucopyranosyl-(1->4)-6-D-galactose, maltotetraose (α-D-glucopyranosyl-(1->4)-α-D-glucopyranosyl-(1->4)-α-D-glucopyranosyl-(1->4)-D-glucose), and stachyose (β-D-fructofuranosyl=α-D-galactopyranosyl-(1->6)-α-D-galactopyranosyl-(1->6)-α-D-glucopyranoside); pentasaccharide compounds such as maltopentaose (α-D-glucopyranosyl-(1->4)-α-D-glucopyranosyl-(1->4)-α-D-glucopyranosyl-(1->4)-α-D-glucopyranosyl-(1->4)-D-glucose, and verbascose (β-D-fructofuranosyl-α-D-galactopyranosyl-(1->6)-α-D-galactopyranosyl-(1->6)-α-D-galactopyranosyl-(1->6)-α-D-glucopyranoside; and hexasaccharide compounds such as maltohexaose (α-D-glucopyranosyl-(1->4)-α-D-glucopyranosyl-(1->4)-α-D-glucopyranosyl-(1->4)-α-D-glucopyranosyl-(1->4)-α-D-glucopyranosyl-(1->4)-D-glucose), but the oligosaccharide compound is not limited to these.

Oligosaccharide compounds as trimer to hexamer of glucose can be preferably used, and oligosaccharide compounds as trimer or tetramer of glucose can be more preferably used. More specifically, isomalttriose, isopanose, maltotriose, maltotetraose, maltopentaose, maltohexaose, and the like can be preferably used, and among these, maltotriose, maltotetraose, maltopentaose, and maltohexaose consisting of glucose units linked through α1-4 linkages are more preferred. Particularly preferred are maltotriose and maltotetraose, and most preferred is maltotriose. Although amount of the oligosaccharide compound used for the surface modification of the lipid membrane structure is not particularly limited, it is, for example, about 1 to 30 mol %, preferably about 2 to 20 mol %, more preferably about 5 to 10 mol %, based on the total amount of lipids.

Although the method for modifying the surface of the lipid membrane structure with the oligosaccharide compound is not particularly limited, for example, since liposomes consisting of lipid membrane structures of which surfaces are modified with monosaccharides such as galactose and mannose are known (International Patent Publication WO2007/102481), the surface modification method described in this publication can be employed. The entire disclosure of the aforementioned publication is incorporated into the disclosure of this specification by reference. This means is a method of binding a monosaccharide compound to polyalkylene glycolated lipids to perform surface modification of lipid membrane structures. Since surfaces of lipid membrane structures can be simultaneously modified with polyalkylene glycol by this means, it is preferred.

Blood retainability of a liposome can be enhanced by modifying the surface of the lipid membrane structure as the liposome with a hydrophilic polymer such as polyalkylene glycol. This means is described in, for example, Japanese Patent Unexamined Publication (KOKAI) Nos. 1-249717, 2-149512, 4-346918, 2004-10481, and the like As the hydrophilic polymer, a polyalkylene glycol is preferred. As the polyalkylene glycol, for example, polyethylene glycol, polypropylene glycol, polytetramethylene glycol, polyhexamethylene glycol, and the like can be used. Molecular weight of the polyalkylene glycol is, for example, about 300 to 10,000, preferably about 500 to 10,000, more preferably about 1,000 to 5,000.

The surface modification of the lipid membrane structure with a polyalkylene glycol can be easily performed by constructing the lipid membrane structure using, for example, a polyalkylene glycol-modified lipid as a lipid membrane-constituting lipid. For example, when the modification with a polyethylene glycol is performed, stearylated polyethylene glycols (for example, PEG45 stearate (STR-PEG45) and the like) can be used. In addition, polyethylene glycol derivatives, such as N-{carbonyl-methoxypolyethylene glycol 2000}-1,2-dipalmitoyl-sn-glycero-3-phosphoethanolamine, n-{carbonyl-methoxypolyethylene glycol 5000}-1,2-dipalmitoyl-sn-glycero-3-phosphoethanolamine, N-{carbonyl-methoxypolyethylene glycol 750}-1,2-distearoyl-sn glycero-3-phosphoethanolamine, N-{carbonyl-methoxypolyethylene glycol 2000}-1,2-distearoyl-sn-glycero-3-phosphoethanolamine, and N-{carbonyl-methoxypolyethylene glycol 5000}-1,2-distearoyl-sn-glycero-3-phosphoethanolamine, can also be used. However, the polyalkylene glycolated lipid is not limited to these.

The surface modification of the lipid membrane structure can also be performed with, for example, the aforementioned polypeptide (a) and/or polypeptide (b) modified with a polyalkylene glycol. For example, the aforementioned polypeptide (a) and/or polypeptide (b) modified with a polyalkylene glycol condensed with an appropriate phospholipid, for example, a stearylated polyethylene glycol, can be used. For example, it is preferable to use a polypeptide in which a polyalkylene glycol is condensed to a cysteine (Cys) residue at the N- or C-terminus. In this embodiment, the modifications of the lipid membrane with a polyalkylene glycol and the aforementioned polypeptide (a), and/or polypeptide (b) can be simultaneously attained.

Further, by binding an oligosaccharide compound to the polyethylene glycol, surface modification with a polyalkylene glycol and surface modification with an oligosaccharide compound can also be simultaneously attained. However, the method for modifying the surface of the lipid membrane structure with a polyalkylene glycol or an oligosaccharide compound is not limited to the aforementioned method. For example, the surface modification may be performed by using a lipidated compound such as a stearylated polyalkylene glycol or oligosaccharide compound as a constituent lipid of the lipid membrane structure.

As lipid derivatives for enhancing retainability in blood used for the preparation of the lipid membrane structure of the present invention, for example, glycophorin, ganglioside GM1, phosphatidylinositol, ganglioside GM3, glucuronic acid derivative, glutamic acid derivative, polyglycerin-phospholipid derivative, and the like can be used. As hydrophilic polymer for enhancing retainability in blood, besides polyalkylene glycol, dextran, pullulan, Ficoll, polyvinyl alcohol, styrene-maleic anhydride alternating copolymer, divinyl ether-maleic anhydride alternating copolymer, amylose, amylopectin, chitosan, mannan, cyclodextrin, pectin, carrageenan, and the like can also be used for the surface modification.

In order to efficiently extricate the lipid membrane structure from the inside of the endosome into the cytoplasm, the lipid membrane of the lipid membrane structure of the present invention may be modified with GALA. For example, since liposomes of which surfaces are modified with GALA are described in Japanese Patent Unexamined Publication (KOKAI) No. 2006-28030, the lipid membrane structure of which surface is modified with GALA can be easily prepared according to the method described in the aforementioned publication. In general, by preparing a lipid membrane structure using a cholesterol derivative of GALA (Chol-GALA) as a lipid component, a lipid membrane structure of which surface is modified with GALA can be prepared. Although amount of GALA used for the surface modification of the lipid membrane structure is not particularly limited, it is, for example, about 0.01 to 10 mol %, preferably about 0.1 to 4 mol %, more preferably about 1 to 3 mol %, based on the total amount of lipids.

The term "GALA" referred to in this specification include the peptide specified by SEQ ID NO: 1 mentioned in Sequence Listing of Japanese Patent Unexamined Publication (KOKAI) No. 2006-28030, as well as a modified peptide thereof having the amino acid sequence of the aforementioned peptide, but including deletion, substitution and/or addition of one or several amino acid residues, and having substantially the same properties as those of GALA (for example, a property that it can fuse lipid membranes under an acid condition). The term "GALA" used in this specification should not be construed in any limitative way. As for GALA and method for surface modification of a lipid membrane structure with GALA, the entire disclosure of Japanese Patent Unexamined Publication (KOKAI) No. 2006-28030 is incorporated into the disclosure of this specification by reference.

Surface of the lipid membrane structure of the present invention may also be modified with an MPC polymer. The MPC polymer is an MPC polymer obtainable by polymerizing 2-methacryloyloxyethylphosphorylcholine (MPC). It has been demonstrated that, since this polymer has a molecular structure similar to that of biomembranes, it scarcely shows interactions with biological substances such as polypeptides and hemocytes, and shows superior biocompatibility. In this specification, the term "MPC polymer" is used for referring to both a homopolymer of MPC and a copolymer of MPC and another polymerization component.

As the MPC polymer, commercial polymers can be easily obtained. For example, a homopolymer of MPC (CAS: 67881-99-6); a copolymer of MPC with butyl methacrylate (CAS: 125275-25-4); a terpolymer of MPC, sodium methacrylate and butyl methacrylate; a bipolymer of MPC and 2-hydroxy-3-(meth)acryloyloxypropyltrimethylammonium chloride; a phospholipid polymer (LIPIDURE-S), and the like are provided by NOF Corporation with the registered trademark of "LIPIDURE", and any of these can be used for the present invention.

Although type of the MPC polymer used for the present invention is not particularly limited, for example, a copolymer of MPC and a methacrylic acid ester such as butyl methacrylate, especially such a block copolymer, and the like can be preferably used. The preparation method of this copolymer is described in detail in Japanese Patent No. 2890316, and those skilled in the art can easily prepare a desired copolymer by referring to this patent publication. The entire disclosure of this patent publication is incorporated into the disclosure of this specification by reference. In the present invention, an MPC polymer showing water solubility and having a hydrophobic group is preferably used. From this point of view, an MPC copolymer prepared by using an acrylic acid ester or methacrylic acid ester having about 4 to 18 carbon atoms can be preferably used. As a copolymer of MPC and butyl methacrylate (BMA), for example, a copolymer having a molar ratio of MPC and BMA of 5:5 (PMB50), a copolymer having a molar ratio of MPC and BMA of 3:7 (PMB30), and the like are known, and it can be easily prepared according to, for example, the method described in Polymer Journal, 22, pp. 355-360, 1990, or the like (specific preparation methods are explained in, for example, Japanese Patent Unexamined Publication (KOKAD No. 2007-314526). For the present invention, PMB50 can be most preferably used. Although degree of polymerization and molecular weight of the MPC polymer are not particularly limited, a polymer having an average molecular weight (weight average molecular weight) of, for example, about 5,000 to 300,000, preferably about 10,000 to 100,000, can be used from a viewpoint of maintaining water solubility.

Although the method for modifying the lipid membrane structure with the MPC polymer is not particularly limited, for example, an MPC polymer can be added to an aqueous dispersion of the lipid membrane structure such as liposomes, and the mixture can be left at room temperature for about several minutes to several hours. Although amount of the MPC polymer to be added to the aforementioned aqueous dispersion is not particularly limited, it may be added in an amount corresponding to the amount of the MPC polymer used for the modification, for example, 0.01 to 1 mass %, preferably about 0.1 to 10 mass %, more preferably about 0.1 to 3 mass %, based on the total amount of lipids of the lipid membrane structure. By this operation, the MPC polymer is quickly taken up into the lipid components of the lipid membrane structure, and the lipid membrane structure of which surface is modified with the MPC polymer can be prepared. Although amount of the MPC polymer used for the surface modification is not particularly limited, it is, for example, in the range of about 0.1 to 5 mass % based on the total amount of lipids of the lipid membrane structure.

The lipid membrane structure of the present invention may contain one or two or more kinds of substances selected from the group consisting of a membrane stabilization agent such as sterol, glycerol, and a fatty acid ester thereof, an antioxidant such as tocopherol, propyl gallate, ascorbyl palmitate, and butylated hydroxytoluene, a chargeable substance, a membrane polypeptide, and the like. Examples of the chargeable substance that imparts positive charge include saturated or unsaturated fatty amines such as stearylamine and oleylamine; saturated or unsaturated synthetic cationic lipids such as dioleoyltrimethylammonium propane; cationic polymers, and the like, and examples of the chargeable substance that imparts negative charge include, for example, dicetyl phosphate, cholesteryl hemisuccinate, phosphatidylserine, phosphatidylinositol, phosphatidic acid, and the like. Examples of the membrane polypeptide include, for example, extrinsic membrane polypeptides, integral membrane polypeptides, and the like. Amounts of these substances to be added are not particularly limited, and can be appropriately chosen depending on the purpose.

Further, the lipid membrane structure of the present invention may be imparted with one or two or more functions selected from, for example, temperature change sensing function, membrane permeating function, gene expressing function, pH sensing function, and the like. By appropriately imparting these functions, retainability in blood of the lipid membrane structure encapsulating, for example, a nucleic acid containing a gene or the like can be improved, a rate of capture by reticuloendothelial systems of liver, spleen and the like can be reduced, the lipid membrane structure can be efficiently extricated from the endosome and transferred to the nucleus after endocytosis of a target cell, and it becomes possible to attain high gene expression activity in the nucleus.

Examples of temperature change-sensitive lipid derivatives that can impart the temperature change sensing function include, for example, dip almitoylphosphatidylcholine and the like. Examples of pH-sensitive lipid derivatives that can impart the pH sensing function include, for example, dioleoylphosphatidylethanolamine and the like.

Further, the lipid membrane structure of the present invention may also be modified with a substance that can specifically bind with a receptor or antigen on the surface of a cell, such as antibodies, to improve efficiency of delivery of a substance into the nucleus. For example, a monoclonal antibody directed to a biological component specifically expressed in a target tissue or organ is preferably disposed on the surface of the lipid membrane structure. This technique is described in, for example, STEALTH LIPOSOME (pages 233 to 244, published by CRC Press, Inc., edited by Danilo Lasic and Frank Martin) and the like As a component of the lipid membrane structure, there can be contained a lipid derivative that can react with mercapto group in a monoclonal antibody or a fragment thereof (e.g., Fab fragment, F(ab')$_2$ fragment, Fab' fragment and the like), specifically, a lipid derivative having a maleinimide structure such as poly(ethylene glycol)-α-distearoylphosphatidylethanolamine-ω-maleinimide and α-[N-(1,2-distearoyl-sn-glycero-3-phosphorylethyl)carbamyl]-ω-{3-[2-(2,5-dihydro-2,5-dioxo-1H-pyrrol-1-yl)ethanecarboxamido]propyl}-poly(oxy-1,2-ethanediyl), and thereby the monoclonal antibody can be bound to the surface of the membrane of the lipid membrane structure.

Surface of the lipid membrane structure of the present invention may be modified with a polypeptide containing a plurality of contiguous arginine residues (henceforth referred to as "polyarginine"). As the polyarginine, preferably a polypeptide containing 4 to 20 contiguous arginine residues (SEQ ID NO: 3), more preferably a polypeptide consisting only of 4 to 20 contiguous arginine residues (SEQ ID NO: 3), most preferably octaarginine (SEQ ID NO: 4), and the like can be used. By modifying the surface of a lipid membrane structure such as liposome with a polyarginine such as octaarginine (SEQ ID NO: 4), intracellular delivery efficiency of a target substance enclosed in liposome can be improved (Journal of Controlled Release, 98, pp.317-323, 2004; International Patent Publication WO2005/32593). Surface of the lipid membrane structure can be easily modified with a polyarginine according to the method described in the aforementioned publications using, for example, a lipid-modified polyarginine such as stearylated octaarginine (SEQ ID NO: 4) as a constituent lipid of the lipid membrane structure. The disclosures of the aforementioned publications and the disclosures of all of the references cited in the publications are incorporated into the disclosure of this specification by reference.

Surface of the lipid membrane structure of the present invention may be modified with a polypeptide containing a plurality of contiguous arginine residues (henceforth referred to as "polyarginine"). As the polyarginine, preferably a polypeptide containing 4 to 20 contiguous arginine residues, more preferably a polypeptide consisting only of 4 to 20 contiguous arginine residues, most preferably octaarginine, and the like can be used. By modifying the surface of a lipid membrane structure such as liposome with a polyarginine such as octaarginine, intracellular delivery efficiency of a target substance enclosed in liposome can be improved (Journal of Controlled Release, 98, pp. 317-323, 2004; International Patent Publication WO2005/32593). Surface of the lipid membrane structure can be easily modified with a polyarginine according to the method described in the aforementioned publications using, for example, a lipid-modified polyarginine such as stearylated octaarginine as a constituent lipid of the lipid membrane structure. The disclosures of the aforementioned publications and the disclosures of all of the references cited in the publications are incorporated into the disclosure of this specification by reference.

Furthermore, surface of the lipid membrane structure of the present invention may be modified with INF7. INF7 is a glutamic acid-rich peptide obtained by modifying a peptide (1-23) derived from the influenza HA polypeptide (HA2), and it has been reported that the lipid structure of liposomes is collapsed in the presence of INF7, and a substance enclosed in the liposomes is easily released (Biochemistry, 46, pp. 13490-13504, 2007). There has also been proposed a delivery system comprising polyethylene glycol tetraacrylate (PEG-TA) bound with INF7 (The Journal of Gene Medicine, 10, pp. 1134-1149, 2008). Those skilled in the art can easily use INF7 in the present invention by referring to these publications. The term "INF7" used in this specification is used to refer to the peptide specified by the sequence described in Biochemistry, 46, pp. 13490-13504, 2007, Table 1, as well as a modified peptide thereof having the amino acid sequence of the aforementioned peptide, but including deletion, substitution and/or addition of one or several amino acid residues, and having substantially the same properties as those of INF7. The term "INF7" used in this specification should not be construed in any limitative way. The disclosures of the aforementioned publications and the disclosures of all of the references cited in these publications are incorporated into the disclosure of this specification by reference.

Although the method for modifying the lipid membrane structure with INF7 is not particularly limited, the lipid membrane structure of which surface is modified with INF7 can generally be easily prepared by constructing the lipid membrane structure by using a lipid-modified INF7 comprising a lipid compound and INF7 covalently bound with each other as a lipid membrane constituent lipid. As the lipid-modified INF, for example, stearylated INF7 and the like can be used. This compound can be easily prepared according to the method described in Futaki, S. et al., Bioconjug. Chem., 12 (6), pp. 1005-1011, 2001. Although amount of INF7 used for the surface modification is not particularly limited, it is generally in the range of 1 to 5 mole %, preferably about 3 to 5 mole %, based on the total amount of lipids of the lipid membrane structure.

A multifunctional envelope-type nano device (MEND) is known, and it can be preferably used as the lipid membrane structure of the present invention. MEND has, for example, a structure that it contains a complex of a nucleic acid such as plasmid DNA and a cationic polymer such as protamine as a core, and the core is enclosed in the inside of a lipid envelope membrane in the form of liposome. On the lipid envelope membrane of MEND, a peptide for adjusting pH responding property and membrane permeability can be disposed as required, and the external surface of the lipid envelope membrane can be modified with an alkylene glycol such as polyethylene glycol. Condensed DNA and the cationic polymer are enclosed in the inside of the lipid envelope of MEND, and it is designed so that gene expression can be efficiently attained. As MEND suitably used for the present invention, MEND in which a complex of a plasmid DNA incorporated with a desired gene and protamine is enclosed in the inside, and the outer surface of the lipid envelope is modified with an oligosaccharide-bound PEG is preferred. For the modification with the oligosaccharide-bound PEG, it is preferable to use stearylated polyethylene glycol bound with the polypeptide (a) and/or the polypeptide (b) mentioned above as a constituent lipid component. As for MEND, for example, references for general remarks, such as Drug Delivery System, 22-2, pp. 115-122, 2007, can be referred to. The disclosure of the aforementioned publication and the disclosures of all of the references cited in this publication are incorporated into the disclosure of this specification by reference.

Although form of the lipid membrane structure is not particularly limited, examples include, for example, a dispersion in an aqueous solvent (for example, water, physiological saline, phosphate buffered physiological saline, and the like), a lyophilized product of the aqueous dispersion, and the like.

The method for preparing the lipid membrane structure is not particularly limited, either, and an arbitrary method available for those skilled in the art can be employed. For example, the lipid membrane structure can be prepared by dissolving all the lipid components in an organic solvent such as chloroform, forming a lipid membrane by exsiccation under reduced pressure in an evaporator or spray drying using a spray dryer, then adding an aqueous solvent to the aforementioned dried mixture, and emulsifying the mixture with an emulsifier such as homogenizer, an ultrasonic emulsifier, a high pressure injection emulsifier, or the like. Further, it can be prepared by a method well known as a method for preparing liposomes, for example, the reverse phase evaporation method, and the like. When it is desired to control the size of the lipid membrane structure, extrusion (extrusion filtration) can be performed under high pressure by using a membrane filter having pores of uniform diameters, or the like. Although size of the dispersed lipid membrane structure is not particularly limited, in the case of liposome, for example, particle size is about 50 nm to 5 µm, preferably about 50 nm to 400 nm, more preferably 50 nm to 300 nm, still more preferably 150 nm to 250 nm. The particle size can be measured by, for example, the DLS (dynamic light scattering) method.

The composition of the aqueous solvent (dispersion medium) is not particularly limited, and examples include, for example, a buffer such as phosphate buffer, citrate buffer, and phosphate-buffered physiological saline, physiological saline, a medium for cell culture and the like. Although the lipid membrane structure can be stably dispersed in these aqueous solvents (dispersion media), the solvents may be further added with a saccharide (aqueous solution), for example, a monosaccharide such as glucose, galactose, mannose, fructose, inositol, ribose and xylose, a disaccharide such as lactose, sucrose, cellobiose, trehalose and maltose, a trisaccharide such as raffinose and melezitose, and polysaccharide such as cyclodextrin, a sugar alcohol such as erythritol, xylitol, sorbitol, mannitol, and maltitol, or a polyhydric alcohol (aqueous solution) such as glycerin, diglycerin, polyglycerin, propylene glycol, polypropylene glycol, ethylene glycol, diethylene glycol, triethylene glycol, polyethylene glycol, ethylene glycol mono-alkyl ether, diethylene glycol mono-alkyl ether and 1,3-butylene grycol. In order to stably store the lipid membrane structure dispersed in such an aqueous solvent for a long period of time, it is desirable to minimize electrolytes in the aqueous solvent from a viewpoint of physical stability such as prevention of aggregation. Further, from a viewpoint of chemical stability of lipids, it is desirable to control pH of the aqueous solvent to be in a range of from weakly acidic pH to around neutral pH (around pH 3.0 to 8.0), and/or to remove dissolved oxygen by nitrogen bubbling or the like.

When the resulting aqueous dispersion of the lipid membrane structure is lyophilized or spray-dried, use of a saccharide (aqueous solution), for example, a monosaccharide such as glucose, galactose, mannose, fructose, inositol, ribose and xylose, a disaccharide such as lactose, sucrose, cellobiose, trehalose and maltose, a trisaccharide such as raffinose and melezitose, a polysaccharide such as cyclodextrin, a sugar alcohol such as erythritol, xylitol, sorbitol, mannitol, and maltitol or the like may improve stability. When the aforementioned aqueous dispersion is frozen, use of the aforementioned saccharide or a polyhydric alcohol (aqueous solution) such as glycerin, diglycerin, polyglycerin, propylene glycol, polypropylene glycol, ethylene glycol, diethylene glycol, triethylene glycol, polyethylene glycol, ethylene glycol mono-alkyl ether, diethylene glycol mono-alkyl ether and 1,3-butylene glycol may improve stability.

In the inside of the lipid membrane structure of the present invention, for example, liposome, a substance to be delivered to the inside of a nucleus of a cell in a target tissue or organ can be enclosed. Although type of the substance to be enclosed is not particularly limited, active ingredients of arbitrary medicaments such as antitumor agent, anti-inflammatory agent, antimicrobial agent, and antiviral agent as well as other arbitrary substances such as saccharides, peptides, nucleic acids, low molecular weight compounds, and metallic compounds can be enclosed. Examples of the nucleic acid include a nucleic acid containing a gene, and specific examples include, for example, a gene incorporated into a plasmid. However, the nucleic acid is not limited to these specific examples. Further, it is of course that arbitrary genes can be used as the gene. Although a case of enclosing a nucleic acid will be specifically explained below as an example of the present invention, the scope of the present invention is not limited to this specific embodiment.

In the lipid membrane structure of the present invention, a nucleic acid can be preferably enclosed. The nucleic acid includes DNA and RNA, as well as analogues and derivatives thereof (for example, peptide nucleic acid (PNA), phosphorothioate DNA, and the like). The nucleic acid may be a single-stranded or double-stranded nucleic acid, and may be a linear or cyclic nucleic acid. The nucleic acid may contain a gene. The gene may be any of oligonucleotide, DNA, and RNA, and in particular, genes for in vitro induction such as transformation, genes acting after in vivo expression thereof, for example, genes for gene therapies such as normal genes for homologous recombination, and the like can be mentioned. As the nucleic acid for therapeutic treatment, antisense oligonucleotide, antisense DNA, antisense RNA, and a gene encoding an enzyme or a physiologically active substance such as cytokine, as well as a nucleic acid having a function of controlling gene expression, for example, a functional nucleic acid including RNA such as siRNA can also be used, and these are also encompassed within the scope of the term "nucleic acid" used in this specification. The term "nucleic acid" used in this specification must be construed in its broadest sense, and it should not be construed in any limitative way. For example, when a DNA is used as the nucleic acid, for example, a gene DNA to be expressed can be ligated to a vector DNA, and encapsulated in the lipid membrane structure. However, in order to attain further higher gene expression efficiency, it is preferred that the vector DNA does not contain any CpG sequence, and it may be more preferred that, in addition to the above, the gene DNA to be expressed does not contain any CpG sequence. It is preferred that an enhancer and/or a promoter is ligated to the vector.

Further, when a nucleic acid is enclosed in the lipid membrane structure of the present invention, a compound having a nucleic acid-introducing function can also be added. Examples of such a compound include, for example, O,O'—N-didodecanoly-N-(α-trimethylammonioacetyl)-diethanolamine chloride, O,O'—N-ditetradecanoly-N-(α-trimethylammonioacetyl)-diethanolamine chloride, O,O'—N-dihexadecanoly-N-(α-trimethylammonioacetyl)-diethanolamine chloride, O,O'—N-dioctadecenoyl-N-(α-trimethylammonioacetyl)-diethanolamine chloride, O,O',O"-tridecanoly-N-(ω-trimethylammoniodecanoyl) aminomethane bromide, N-[α-trimethylammonioacetyl]-didodecyl-D-glutamate, dimethyldioctadecylammonium bromide, 2,3-dioleyloxy-N-[2-(sperminecarboxamido)ethyl]-N,N-dimethyl-1-propane ammonium trifluoroacetate, 1,2-dimyristyloxypropyl-3-dimethyl-hydroxyethylammonium bromide, 3-β-[N—(N',N'-dimethylaminoethane)carbamoyl]cholesterol, and the like. These compounds having a nucleic acid-introducing function may be disposed at an arbitrary position of the membrane of the lipid membrane structure, and/or filled in the inside of the lipid membrane structure.

For example, the lipid membrane structure encapsulating a nucleic acid can be used as a carrier for delivering the nucleic acid into a nucleus of a cell of a target tissue or organ. When aiming at gene expression, it is particularly preferable to use a nucleic acid containing a desired gene as the nucleic acid and the aforementioned MEND. For example, by administering a lipid membrane structure, preferably MEND, enclosing a nucleic acid containing a gene to a mammal including human, a desired gene can be delivered into nuclei of cells of a target tissue or organ, and efficiently expressed. Although administration method is not particularly limited, parenteral administration is preferred, and intravenous administration is more preferred. When the lipid membrane structure of the present invention is used as a medicament, for example, a medicament in the form of a pharmaceutical composition can be prepared with appropriate pharmaceutical additives and administered.

When a nucleic acid is introduced into a nucleus of an immunocyte, preferably dendritic cell, by using the lipid membrane structure of the present invention, the encapsulated substance, i.e., the nucleic acid, is efficiently released in the nucleus to induce expression of a polypeptide encoded by the nucleic acid. Where a nucleic acid encoding a polypeptide is introduced into the nucleus of dendritic cell by using the lipid membrane structure of the present invention, the polypeptide transcribed and translated from the nucleic acid is presented on the surface of the dendritic cell, and the living host can acquire immunity against the polypeptide. Therefore, it becomes possible to perform effective immunotherapy against any desired polypeptide. This embodiment is a particularly preferred embodiment of the present invention.

Further, the lipid membrane structure provided by the present invention itself can exhibit an adjuvant action for dendritic cells and promote production of various cytokines. Therefore, by using the lipid membrane structure of the present invention, immunotherapy can be highly efficiently performed. Further, by administering dendritic cells transformed with the lipid membrane structure provided by the present invention to a mammal including human, exacerbation or proliferation of tumor can be remarkably suppressed irrespective of the presence or absence of adjuvant, and when the lipid membrane structure encapsulating an antigen protein is administered, cytotoxicity can be enhanced in vivo. Therefore, the lipid membrane structure can be used as a highly effective active ingredient of a vaccine for prophylactic treatment of malignant tumor or a medicament for therapeutic treatment of malignant tumor.

EXAMPLES

Hereafter, the present invention will be more specifically explained with reference to examples. However, the scope of the present invention is not limited to the following examples.

Example 1

(a) Preparation of Nucleic Acid to be Enclosed (Aggregate Formed with Protamine)

A plasmid encoding luciferase (pDNA, BD Biosciences Clontech) was dissolved in a 10 mM HEPES buffer at a concentration of 0.1 mg/mL. A 0.1 mg/mL solution of protamine (150 μL, 10 mM HEPES buffer) was dropped portionwise with the pDNA solution (100 μL) with stirring to prepare a compaction body of protamine and the pDNA (N/P ratio was 2.2).

(b) Preparation of Protamine Core-Enclosed Liposomes

A 1 mM solution of DOPE (112.5 μl) and a 1 mM solution of CHEMS (25 μl) were put into a glass test tube so as to obtain a DOPE:CHEMS ratio of 9:2. The mixture was added with a 1 mg/mL solution of Chol-GALA (SEQ ID NO: 13) synthesized according to the method described in Biochemistry, 43, pp.5618-5628, 2004, and a 1 mg/mL solution of stearylated KALA (SEQ ID NO: 1) (STR-KALA) synthesized according to the method described in Japanese Patent Unexamined Publication (KOKAI) No. 2003-343857 in volumes for modifying 1 to 8% of the total lipids, and further added with chloroform to a total volume of 200 μl, and the mixture was dried under reduced pressure in a desiccator to evaporate the solvent and thereby obtain a lipid membrane. This lipid membrane was added with the compaction body prepared in the section (a) mentioned above so that the total lipid concentration became 0.55mM, and the mixture was left standing at room temperature for 10 minutes to allow hydration, and then ultrasonicated for 1 minute with a sonicator. The mixture was added with stearylated octaarginine (SEQ ID NO: 4) (STR-R8) synthesized according to the method described in Japanese Patent Unexamined Publication (KOKAI) No. 2003-343857 (2mg/mL aqueous solution) in such a volume that the added STR-R8 amount corresponded to 5mol % of the total lipids, and the mixture was left standing at room temperature for 10 minutes.

(c) Preparation of Nucleic Acid to be Enclosed (Aggregate Formed with Polyrotaxane)

A plasmid encoding luciferase (pDNA, BD Biosciences Clontech) was dissolved in a 10 mM HEPES buffer at a concentration of 0.1 mg/mL. Polyrotaxane synthesized according to the method described in J. Control. Release, 131, pp. 137-144, 2008 (average polyethylene glycol chain length: 4,000, number of threaded cyclodextrin: 29, average number of cations in one chain: 46) was dissolved in a 10 mM HEPES buffer (1 mM in terms of amine concentration), and the resulting solution (150 µL) was dropped portionwise with the pDNA solution (100 µL) with stirring to prepare a compaction body of polyrotaxane and pDNA (N/P ratio was 5.0).

(d) Preparation of Polyrotaxane Core-Enclosed Liposomes

A 1 mM solution of DOPE (107µL) and a 1 mM solution of phosphatidic acid (PA, 25 µL) were put into a glass test tube so as to obtain a DOPE:PA ratio of 7:2. The mixture was added with a 1mg/mL solution of STR-KALA (SEQ ID NO: 1), synthesized according to the method described in Japanese Patent Unexamined Publication (KOKAI) No. 2003-343857, in a volume for modifying 1.5 to 5% of the total lipids (8.25to 27.5µL), and further added with chloroform to a total volume of 200 µL, and then the mixture was dried under reduced pressure in a desiccator to evaporate the solvent and thereby obtain a lipid membrane. This lipid membrane was added with the compaction body prepared in the section (c) mentioned above so that the total lipid concentration became 0.55 mM, and the mixture was left standing at room temperature for 10 minutes to allow hydration, and then ultrasonicated for 1 minute with a sonicator. The mixture was added with a 2 mg/mL aqueous solution of stearylated octaarginine (SEQ ID NO: 4) (STR-R8) synthesized according to the method described in Japanese Patent Unexamined Publication (KOKAI) No. 2003-343857in such a volume that the added STR-R8amount corresponded to 10 mol % of the total lipids, and the mixture was left standing at room temperature for 10 minutes for hydration.

(e) Preparation of Transformed Cells

The JAWS II cells were inoculated on a 24-well plate at a density of $8 \times 10^4$ cells/well, and cultured for 24 hours in the αMEM medium. After the cultured cells were washed with 500 µL of PBS, the liposomes prepared in the sections (b) and (d) mentioned above, and control liposomes (not modified with stearylated KALA and Chol-GALA) were each added to αMEM so that a pDNA amount of 0.4 µg/well was to be obtained, the mixture was added to each well, and incubation was performed at 37° C. and 5% $CO_2$ for 3 hours. After the incubation, the cells were washed with 500 µL of PBS, then 1 mL of αMEM was added to each well, and incubation was further performed under the conditions of 37° C. and 5% $CO_2$ for 21 hours to prepare transformed cells.

(f) Measurement of Expression Amount

The transformed cells prepared in the section (e) mentioned above were washed with 500 µL of PBS, this PBS was collected into a 1.5-mL sample tube, and centrifuged (4° C., 2,000 rpm, 2 minutes), and the supernatant was removed. Each well was added with 75 µL of Reporter Lysis Buffer (Promega), and the plate was transferred to a freezer at −80° C. to freeze the cell suspension. After the frozen sample was thawed, the cells were scraped off with a cell scraper, and collected in a 1.5-mL sample tube. A lysate of the collected cells was centrifuged (4° C., 15,000 rpm, 5 minutes), and 45 µL of the supernatant was collected. The luciferase activity (RLU/mL) in the resulting supernatant was measured. Further, proteins were quantified (mg/mL) by the BCA method, the luciferase activity per unit amount of polypeptide (RLU/mg protein) was calculated, and the luciferase expression amounts were compared. Results are shown in FIG. 1.

As shown in FIG. 1, in the case of the liposomes encapsulating the core formed by using protamine with DOPE/CHEMS, when such liposomes modified with Chol-GALA (SEQ ID NO: 13) were used, the gene expression was maximized at a modification amount of 2%, but increase of the gene expression was only about 3 times. Whilst when the liposomes modified with STR-KALA (SEQ ID NO: 1) were used, it was found that the gene expression increased 10times or more, and especially at a modification amount of 5%, the gene expression increased 100times or more. Further, also in the case of the liposomes encapsulating the core formed by using polyrotaxane with lipids of DOPE/PA, when such liposomes modified in a similar manner were used, increase in the gene expression of 10 times or more was observed at the optimal modification amount of 1.5%, compared with the gene expression obtained with those modified only with R8 (SEQ ID NO: 4).

Example 2

(a) Preparation of Positively Charged Core T-MEND

A 3.3 mM solution of cardiolipin (CL, 84 µL) and a 10 mM solution of DOPE (27.5 µL) were put into a glass test tube so as to obtain a CL:DOPE ratio of 1:1. The mixture was added with a 1 mg/mL solution of STR-KALA in a volume for modifying 0.5%, 1%, 2%, or 5% of the total lipids, and further added with chloroform to a total volume of 200 µL, and then the mixture was dried under reduced pressure in a desiccator to evaporate the solvent, and thereby a lipid membrane was obtained. This lipid membrane was added with 1 mL of a 10 mM HEPES solution so that the total lipid concentration became 0.55 mM, and the hydrated lipid membrane was exfoliated from the glass test tube by using a bath type sonicator, and then ultrasonicated for 10 minutes by using a probe type sonicator. After the ultrasonication, centrifugation (15,000 rpm, 20° C., 5 minutes) and collection of supernatant were repeated 3 times to collect four kinds of liposomes (SUV1-1 to 5) of different STR-KALA concentrations.

A 10 mM solution of PA (12.2 µL) and a 10 mM solution of DOPE (42.8 µL) were put into a glass test tube so as to obtain a PA:DOPE ratio of 7:2. The mixture was added with a 1 mg/mL solution of STR-KALA in a volume for modifying 1.5% of the total lipids, and further added with chloroform to a total volume of 200 µL, and then the mixture was dried under reduced pressure in a desiccator to evaporate the solvent, and thereby a lipid membrane was obtained. This lipid membrane was added with 1 mL of a 10 mM HEPES solution so that the total lipid concentration became 0.55 mM, and the hydrated lipid membrane was exfoliated from the glass test tube by using a bath type sonicator, and then ultrasonicated for 10 minutes by using a probe type sonicator. After the ultrasonication, centrifugation (15,000 rpm, 20° C., 5 minutes) and collection of supernatant were repeated 3 times to collect liposomes (SUV2).

The compaction body (100 µL) obtained in Example 1, (c), and a solution of each of SUV1-1 to 5 (200 µL) were mixed in a 1.5-mL sample tube to form five kinds of bilamellar liposomes (D-MEND). After the formation of D-MEND, in order to apply positive charge, a 2 mg/mL solution of STR-R8 was added to each kind of SUV1 liposomes in such a volume that the added STR-R8 amount corresponded to 20 mol % of the total lipid amount of SUV1, and the mixture was incubated at room temperature for about 30 minutes to attain modification with R8.

Further, each solution (200 μL) undergone the above incubation was added with 400 μL of SUV2, and then mixed in a 1.5-mL sample tube to form tetralamellar MEND (T-MEND). Further, T-MEND was added with a 2 mg/mL solution of STR-R8 so that the added STR-R8 amount corresponded to 10 mol % of the total lipid amount of SUV2, and the mixture was incubated at room temperature for about 30 minutes to prepare cationic T-MEND having KALA and R8 on both inner membrane and outer membrane.

(b) Preparation of Negatively Charged Core T-MEND

A plasmid encoding luciferase (pDNA, BD Biosciences Clontech) was dissolved in a 10 mM HEPES buffer at a concentration of 0.1 mg/mL. The 0.1 mg/mL pDNA solution (60 μL) was dropped portionwise with a solution of polyrotaxane (1 mM in terms of amine concentration, 90 μL, average polyethylene glycol chain length: 4,000, number of threaded cyclodextrin: 29, average number of cations in one chain: 46) with stirring to prepare a compaction body of polyrotaxane and pDNA (N/P ratio was 0.5).

A 3.3 mM solution of cardiolipin (CL, 84 μL) and a 10 mM solution of DOPE (27.5 μL) were put into a glass test tube so as to obtain a CL:DOPE ratio of 1:1. The mixture was added with a 2 mg/mL solution of STR-R8 in such a volume that the added STR-R8 amount corresponded to 20 mol % of the total lipid amount, and a 1 mg/mL solution of STR-KALA in such a volume that the added STR-KALA amount corresponded to 0 or 5 mol % of the total lipid amount, and further added with chloroform to a total volume of 200 μL, and then the mixture was dried under reduced pressure in a desiccator to evaporate the solvent, and thereby a lipid membrane was obtained. This lipid membrane was added with 1 mL of a 10 mM HEPES solution so that the total lipid concentration became 0.55 mM, and the hydrated lipid membrane was exfoliated from the glass test tube by using a bath type sonicator, and then ultrasonicated for 10 minutes by using a probe type sonicator. After the ultrasonication, centrifugation (15,000 rpm, 20° C., 5 minutes) and collection of supernatant were repeated 3 times to collect of liposomes (SUV1-0 and 1-5).

A 10 mM solution of PA (12.2 μL) and a 10 mM solution of DOPE (42.8 μL) were put into a glass test tube so as to obtain a PA:DOPE ratio of 7:2. The mixture was added with a 1 mg/mL solution of STR-KALA in a volume for modifying 0 or 1.5% of the total lipids (0 or 8.3 μL), and further added with chloroform to a total volume of 200 μL, and then the mixture was dried under reduced pressure in a desiccator to evaporate the solvent, and thereby two kinds of lipid membranes were obtained. Each lipid membrane was added with 1 mL of a 10 mM HEPES solution so that the total lipid concentration became 0.55 mM, and the hydrated lipid membrane was exfoliated from the glass test tube by using a bath type sonicator, and then ultrasonicated for 10 minutes by using a probe type sonicator. After the ultrasonication, centrifugation (15,000 rpm, 20° C., 5 minutes) and collection of supernatant were repeated 3 times to collect liposomes (SUV2-0 and 2-1.5).

The aforementioned compaction body (100 μL) obtained from pDNA and polyrotaxane at N/P=0.5, and each of the solutions of SUV1-0 and 1-5 (200 μL) were mixed in a 1.5-mL sample tube to form bilamellar liposomes (D-MEND-0 and -5). After the formation of D-MEND, a 2 mg/mL solution of STR-R8 was added to each kind of liposomes in such a volume that the added STR-R8 amount corresponded to 5 mol % of the total lipid amount of SUV1, and the mixture was incubated at room temperature for about 30 minutes.

Further, each solution (D-MEND-0 and -5, 200 μL) undergone the above incubation was added with 400 μL of SUV2-0 or 2-1.5, and mixed in a 1.5-mL sample tube to form tetralamellar MEND (T-MEND). Further, T-MEND was added with a 2 mg/mL solution of STR-R8 in such a volume that the added STR-R8 amount corresponded to 10 mol % of the total lipid amount of SUV2, and the mixture was incubated at room temperature for about 30 minutes to prepare anionic T-MEND having KALA and R8 on both inner membrane and outer membrane.

(c) Preparation of Transformed Cells and Measurement of Expression Amount

Figure 2:
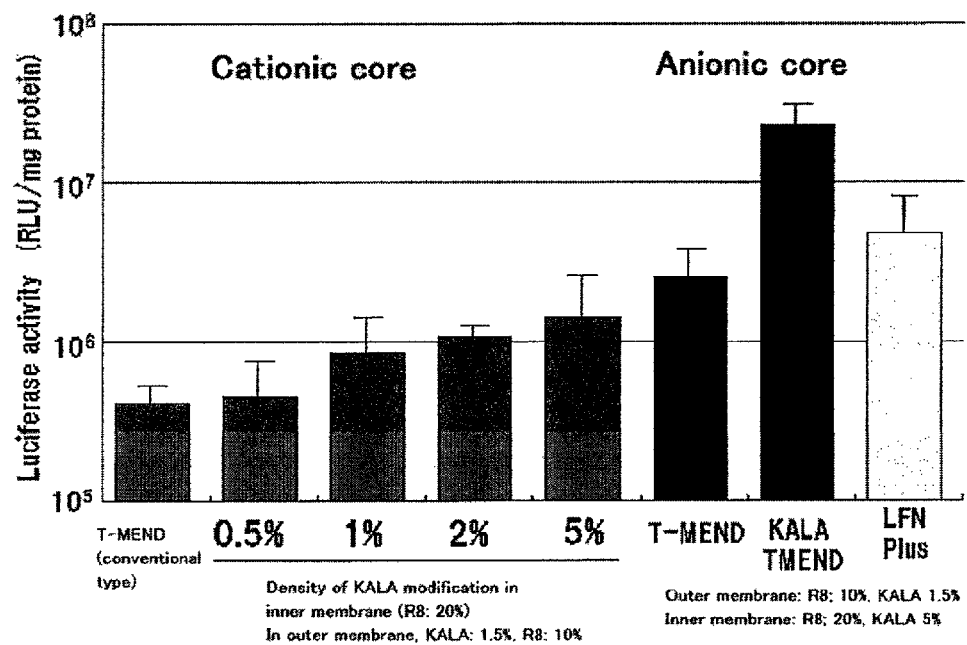
[FIG. 2] This figure depicts gene expression efficiency obtained with tetralamellar cationic T-MEND and anionic T-MEND of which lipid membrane was modified with the polypeptide (a) (KALA) (SEQ ID NO: 1) or with the polypeptide R8 (SEQ ID NO: 4).

Transformed cells were prepared by using the two kinds of T-MEND prepared in the sections (a) and (b) mentioned above according to the method described in Example 1, (e), and expression amount of luciferase in each type of cells was measured according to the method described in Example 1, (f). As a result, in the cationic T-MEND, increase in expression of the encapsulated gene was observed in a KALA modification density-dependent manner (FIG. 2). Further, as also for the anionic T-MEND, the modification of inner membrane and outer membrane with KALA provided 10 times or higher gene expression. In particular, the anionic T-MEND gave gene expression higher than that obtainable with Lipofectamine PLUS, which is a marketed gene transfer reagent.

Example 3

(a) Evaluation of Antigen Presentation Amount

Figure 3:
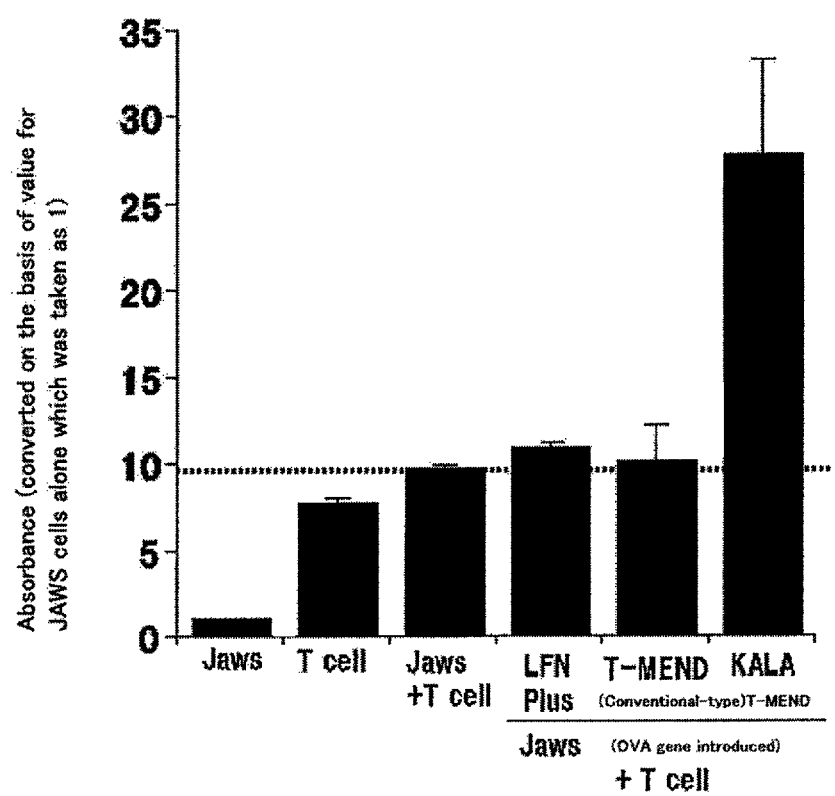
[FIG. 3] This figure depicts the results of presentation of antigen molecules on the surfaces of dendritic cells, which antigen molecules were expressed by introducing a gene encoding the antigen molecule into the nuclei of the dendritic cells using the lipid membrane structure of the present invention.

A plasmid DNA encoding the albumen antigen (ovalbumin) as an antigen was introduced into dendritic cells by using various vectors, and the dendritic cells were collected 24 hours after the transfection, and washed with the medium. Then, $1\times10^4$ cells/100 μL of the dendritic cells and $2\times10^5$ cells/100 μL of the B3Z (MHC-I) cells were inoculated on a 96-well plate, and co-cultivated for 16 hours. Then, the cells were washed with PBS, added with CPRG buffer (100 μL, obtained by dissolving 5 mM CPRG (Roche Diagnostics), 0.125% NP-40 (Igepal CA-630, SIGMA) and 9 mM $MgCl_2$ in redistilled water, dividing the solution into aliquots in a volume of 1 mL each, and the storing the aliquots at −20° C. under light shielding), and incubated at 3'7° C. for 4 hours. Then, absorbance of the culture was measured at 595 nm by using Benchmark Plus Microplate Spectrophotometer (Bio-Rad). The absorbance values were normalized with reference to the value obtained for the medium containing only untreated dendritic cells, which was taken as 1. Results are shown in FIG. 3.

After the ovalbumin gene was introduced, presentation of the antigen was evaluated. As a result, the marketed Lipofectamine PLUS and the conventional type T-MEND failed to provide antigen presentation superior to that obtained in the control (dendritic cells not introduced with the gene, dotted line). Whilst, antigen presentation was observed for the KALA-modified T-MEND that gave the highest gene expression as shown in FIG. 2. From these results, it was demonstrated that the lipid membrane structure of the present invention successfully and highly efficiently introduced the gene into the nuclei of dendritic cells, and the antigen protein expressed from the introduced gene was successfully presented as an antigen on the surfaces of the dendritic cells.

Example 4

Gene Expression Analysis for Immunity-Related Genes Using Microarray Analysis (a) Preparation of R8-MEND and R8/KALA-MEND For preparation of core of vector, each of a pDNA solution and a protamine solution was diluted to 0.1 mg/mL with a 10 mM HEPES buffer. A 0.1 mg/mL solution of protamine (150 µL) was dropped portionwise with a 0.1 mg/mL solution of pDNA (100 µL) with stirring to prepare a compaction body of protamine and pDNA (N/P ratio=2.2). As for lipid membrane, a 1 mM solution of DOPE (112.5 mL) and a 1 mM solution of CHEMS (25 µL) were put into a glass test tube so as to obtain a DOPE:CHEMS ratio of 9:2, the mixture was added with $CHCl_3$ to a total volume of 200 µL, and then the mixture was dried in a desiccator to evaporate the solvent, and thereby a lipid membrane was obtained. This lipid membrane was added with a solution of the compaction body so that the total lipid concentration became 0.55 mM, and added with only STR-R8 in an amount corresponding to 5 mol % of the total lipid amount in the case of R8-MEND, or STR-KALA and STR-R8 in an amount corresponding to 5 mol % of the total lipids in the case of R8/KALA-MEND, and the mixture was left standing at room temperature for 10 minute for hydration, and then ultrasonicated for 1 minute with a sonicator.

(2) Preparation of RNA

Two days before transfection, the JAWS-II cells were inoculated on a 6-well plate at a density of $4\times10^5$ cells/well. The cells were washed with 500 µL of PBS(−), then added with 1 mL of an MEND solution prepared by diluting MEND with αMEM (serum-free, antibiotic-free) to a concentration of 2 µg/mL (in terms of concentration of the plasmid DNA) cell, and left standing at 37° C. in a 5% $CO_2$ incubator. One, three and six hours after the transfection, the cells were washed with 500 µL of PBS(−), and added with TRIzol Reagent (Invitrogen) to a total volume of 1 mL for each sample. The cells were scraped off with a cell scraper, and collected in an Eppendorf tube. The cells were mixed for 1 minute on a vortex mixer and stored at −80° C. For purifying mRNA, each sample was thawed at room temperature, added with 200 µL of chloroform, and mixed for 15 seconds on a vortex mixer. The sample was incubated at room temperature for 3 minutes, and then centrifuged under an environment of 4° C. at 12,000 rpm for 15 minutes. The supernatant was transferred to another Eppendorf tube, and added with 500 µL of isopropanol, and the mixture was incubated at room temperature for 10 minutes. The mixture was centrifuged in an environment of 4° C. at 12,000 rpm for 10 minutes, then the supernatant was removed, the pellet was added with 1 mL of 75% ethanol, and mixed on a vortex mixer, and the mixture was centrifuged (4° C., 12,000 rpm, 4 minutes). The supernatant was removed, the pellet was added with 25 µL of diethyl pyrocarbonate (DEPC)-treated water, the mixture was incubated for 10 minutes, and RNA amount was quantified on the basis of absorbance at 260 nm measured by using Nano Drop (Thermo Scientific).

(3) Labeling of RNA

Labeled RNA for DNA microarray experiment was prepared by using Quick Amp Labeling Kit one-color (Agilent) according to the protocol attached to the kit. cDNA was synthesized from 500 ng of the total RNA by reverse transcription reaction. Then, cRNA labeled with Cyanine 3 (Cy3)-CTP was prepared from the cDNA by in vitro transcription. In order to remove unreacted Cy3, the labeled cRNA was purified by using RNeasy Mini Kit. For the resulting Cy3-labeled cRNA solution, concentration and Cy3 uptake amount were calculated by using NanoDrop to determine the quality.

The Cy3 uptake efficiency of the purified labeled cRNA probe (pmol/µg) was calculated from cRNA concentration (ng/µL) and uptake amount of Cy3 (pmol/µL). The calculation method is shown below.

(1) The cRNA concentration (ng/µL) was calculated in accordance with the following equation.

$$\text{cRNA concentration (ng/µL)} = OD_{260} \times 10^* \times 40 \text{ (µg/mL)}$$

*The optical path length of NanoDrop was 1 mm.

(2) The uptake amount of Cy3 (pmol/µL) was calculated in accordance with the following equation.

$$\text{Cy3 uptake amount (pmol/µL)} = (OD_{550} \times 10^* \times 1000)/(150 \text{ mM}^{-1}\text{cm}^{-1})$$

*The optical path length of NanoDrop was 1 mm.

(3) The Cy3 uptake efficiency (pmol/µg) was calculated in accordance with the following equation.

$$\text{Cy3 uptake efficiency (pmol/µg)} = \text{Cy3 uptake amount (pmol/µL)}/\text{cRNA concentration (ng/µL)}$$

For all the Cy3-labeled cRNA samples, it was confirmed that the yield of cRNA was 1.65 µg or higher, and the Cy3 uptake efficiency was 9 pmol/µg or higher.

(4) DNA Microarray

Hybridization of the labeled cRNA to a mouse oligo-DNA microarray (4×44K) was performed by using Gene Expression Hybridization Kit according to the protocol attached to the kit. The labeled cRNA was randomly digested and thereby fragmented, and a hybridization solution was prepared by using 1.65 µg of RNA. A sample was applied to a microarray slide, hybridization was performed at 65° C. and 17 hours, and then the slide was washed with Expression Wash Buffer containing 10% Triton X-102.

The microarray slide was scanned by using Agilent DNA Microarray Scanner (Agilent Technologies). For the measurement of Cy3, a laser of 532 nm was used. The created TIFF image was read by using Feature Extraction Software, and information of the spots (gene profile) was saved in the form of text file. The resulting expression profile was imported into GeneSpringGX11, and analyzed.

Among the 41220 genes detected as spots, unreliable genes were eliminated (quality control), and thereby 21995 genes usable as the object of analysis (qualified genes) were extracted.

(1) Elimination of Control Spots

When data are imported into the analysis software GeneSpringGX11, control spots including the spots for recognition of the four corners of array are also detected. Therefore these spots were eliminated.

(2) Elimination of Flag

At the time of the detection of spots, flags for three stages, Present (P), Marginal (M), and Absent (A) (reliability decreases in the order of P, M, and A), are evaluated according to the state of signal, for example, disordered shape, saturation of fluorescence, and the like. The genes were extracted to which the evaluation of Present was given for at least one sample among all the samples.

(3) Elimination of Low Expression Gene

Since genes with low expression level might give fluctuation of expression levels even for the same samples, such genes were eliminated. Those genes providing a Raw value of 100 or higher for at least one sample among all the samples were extracted, which value is the absolute value of signal intensity. After the quality control described above was performed, analysis was advanced for the 21995 genes as the object.

Figure 4:
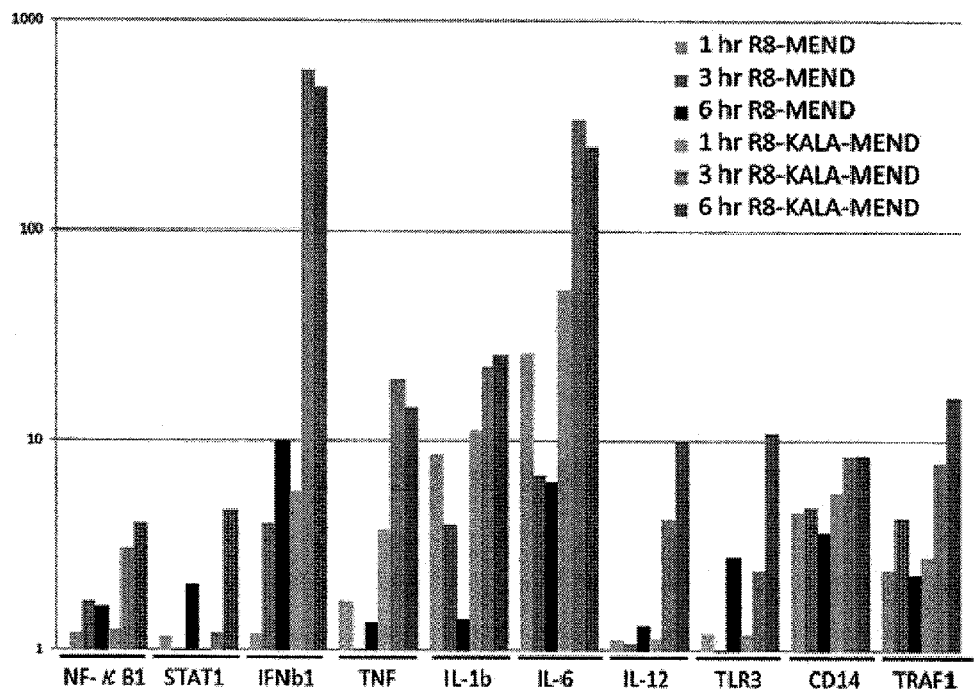
[FIG. 4] This figure depicts the result that KALA (SEQ ID NO: 1) modifying the surface of MEND has an adjuvant effect for dendritic cells. Result with R8 (SEQ ID NO: 4)-modified MEND also shown.

The genes relating to immunity were extracted, and gene expression amounts obtained with R8-MEND and R8/KALA-MEND were compared. The results of this comparison are shown with values of expression amounts of the genes normalized relative to that of untreated cells, which is taken as 1. As a result, it was recognized that the degree of increase in expression of immunity-related genes obtained with R8/KALA-MEND was higher than that obtained with R8-MEND, and the expression of many of the genes increased in a time-dependent manner. From these results, it was revealed that KALA modifying the MEND surface had an adjuvant effect on dendritic cells (FIG. 4).

Example 5

CTL Activity of Protein-Enclosed KALA-modified Liposomes (1) Preparation of Antigen-Enclosed R8-Modified and KALA-modified Liposomes A lipid thin membrane consisting of EPC/Chol/CHEMS (molar ratio: 70:20:10) was prepared in a glass test tube, added with OVA (5 mg/mL, 10 mM HB) so that the lipid concentration became 10 mM, and hydrated at room temperature for 15 minutes. After the hydration, the lipid membrane was mixed on a vortex mixer, transferred to a 15-mL conical tube, frozen and thawed 5 times. The lipid membrane was subjected to extrusion through a membrane filter of 400 nm, the supernatant was removed by ultracentrifugation (43,000 rpm, 4° C., 30 minutes), and then the pellet was gently rinsed with 200 μL of HBG, and suspended again in an appropriate volume of HBG. According to the procedure described in the following section, the OVA concentration and the lipid concentration were determined. Before use in the experiment, the liposomes were added with STR-R8 (10 mg/mL) or STR-KALA (10 mg/mL) in an amount corresponding to 7.5% of the lipid molar concentration, and the mixture was incubated at room temperature for 30 minutes or more to prepare R8-Lip and KALA-Lip. R8-Lip had a particle size of 189.5 nm, PDI of 0.095 and zeta potential of 47.8 mV, and KALA-Lip had a particle size of 188.4 nm, PDI of 0.317, and zeta potential of 33.7 mV.

A liposome solution (25 μL) or OVA for preparation of calibration curve diluted with sterilized water to a volume of 1 mL was added with a 0.15% solution of sodium deoxycholate (100 μL), and the mixture was incubated at room temperature for 10 minutes. The mixture was added with a 72% solution of trichloroacetic acid (100 μL), the mixture was centrifuged (3,500 rpm, 4° C., 20 to 30 minutes), and then the supernatant was removed. The resulting pellet was dissolved in a 0.5% SDS solution in 0.1 N NaOH (50 μL), the solution was added with the BCA assay reagent (1 mL), and quantification was performed according to the protocol. The lipid concentration was determined by using Phospholipid C-Test Wako (Wako Pure Chemical Industries).

(2) CTL (Cytotoxic T Lymphocyte) Activity In Vivo

R8-Lip or KALA-Lip enclosing 50 μg of OVA was subcutaneously administered (26 G needle) to C57BL/6 mice (female, 7 to 9 weeks old). One week after the immunization, target cells prepared by the following method were administered. The spleen was extracted from a naive mouse sacrificed by cervical vertebra dislocation, and the cells were loosened in 3 to 5 mL of the RPMI 1640 medium contained in a petri dish, collected by using a 2.5-mL syringe, then passed through a nylon mesh, and transferred to a 50-mL conical tube. The cells were centrifuged (1600 to 1700 rpm, 4° C., 5 minutes), then the supernatant was removed, and the cells were suspended in 1 mL of the ACK Lysing Buffer (Lonza, Walkersville, Md.), incubated at room temperature for 5 minutes, and thereby hemolyzed. The cell suspension was added with the RPMI 1640 medium (9 mL), then the mixture was centrifuged, and the cells were further washed with the medium (10 mL), then suspended in a volume of 20 mL, passed through a nylon mesh, and transferred to two of 50-mL conical tubes. The cells were counted, centrifuged, and then suspended again in the medium ($10^7$ cells/mL). The cell suspension in one of the tubes were added with $OVA_{257-264}$ peptide (1 mM, final concentration: 5 μM), and this cell suspension was incubated under the conditions of 37° C. and 5% $CO_2$ for 60 minutes. After the cells were washed with medium (10 mL) and PBS (10 mL), the cells pulsed with the $OVA_{257-264}$ peptide were suspended in PBS containing 5 μM of CFSE (Molecular Probe, $CFSE^{High}$), the cells not pulsed with the $OVA_{257-264}$ peptide were suspended in PBS containing 0.5 μM CFSE ($CFES^{Low}$), both at a density of $3\times10^7$ cells/mL, and those cells were incubated at 37° C. for 10 minutes. The cells were washed twice with the RPMI 1640 medium (10 mL) and twice with PBS (10 mL), and finally suspended in PBS ($5\times10^7$ cells/mL). The same amounts of two kinds of the cells stained at different concentrations were mixed immediately before administration, and administered to the immunized mice from the caudal vein ($1\times10^7$ cells/200 μL/mouse, 26 G needle).

Twenty hours after the administration of the target cells, the spleen was extracted, hemolyzed in the same manner as described above, then washed with the RPMI 1640 medium (10 mL) and PBS (10 mL), and suspended in the FACS buffer (5 mL). The prepared cell suspension was passed through a nylon mesh, and transferred to a FACS tube, and number of CFSE-positive cells was measured with a flow cytometer. There were analyzed 7,500 cells stained at a low concentration ($CFSE^{Low}$). The CTL activity was calculated by comparing the cell numbers of $CFSE^{High}$ and $CFSE^{Low}$. Errors between experiments were corrected by using the $CFSE^{High}/CFSE^{Low}$ ratio of the naive mice.

Figure 5:
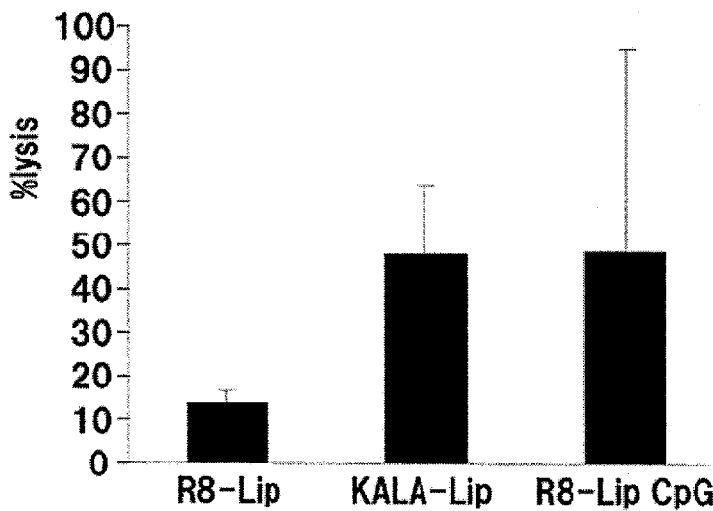
[FIG. 5] This figure depicts the CTL activity of protein-enclosing KALA (SEQ ID NO: 1)-modified liposomes and protein-enclosing R8 (SEQ ID NO: 4)-modified liposomes.

Results are shown in FIG. 5. The vertical axis represents the CTL activity in terms of percentage of killed cell among the cells served as the target of CTL (cells pulsed with the $OVA_{257-264}$ peptide). The cells used as the target ($CFSE^{High}$) presented the OVA peptide as MHO class I presentation, and accordingly, the cell-killing effect observed in this evaluation was provided by OVA-specific CTL.

It has been demonstrated that R8-Lip is a carrier capable of inducing specific MHC class I presentation and antitumor activity in vivo (Nakamura, T. et al., Mol. Ther., 16, pp. 1507-1514, 2008). As shown by the aforementioned results, marked improvement in the CTL activity was provided by modifying the liposome surfaces with KALA instead of R8. Although both R8-Lip and KALA-Lip were used without adjuvant, the CTL activity of KALA-Lip was comparable to the CTL activity obtainable by using R8-Lip carrying a CpG sequence-containing oligonucleotide, which is known as an adjuvant. These results support the results of Example 4 that KALA had high adjuvant function, from the viewpoint of the function.

Example 6

Enhancement of Gene Expression Activity of KALA-MEND by Modification of Vector of Plasmid to be Introduced (a) Preparation of Various Plasmid DNAs The following four kinds of plasmid DNAs were prepared: (1) a plasmid DNA containing CpG sequences in the backbone, and also having CpG sequences in a region from the start codon to the stop codon of the luciferase sequence as a marker gene (pcDNA3.1-Luc(+), 425 CpG sequences in total), (2) a plasmid DNA not containing any CpG sequence in both the backbone and the region from the start codon to the stop codon of the luciferase sequence (pCpGfree-Luc(0), 0 of CpG sequence in total), (3) a plasmid DNA containing CpG sequences in the backbone, but not containing any CpG sequence in the region from the start codon to the stop codon of the luciferase sequence (pcDNA3.1-Luc(0), 332 CpG sequences in total), and (4) a plasmid DNA not containing any CpG sequence in the backbone, but containing CpG sequences in the region from the start codon to the stop codon of the luciferase sequence (pCpGfree-Luc(+), 98 CpG sequences in total).

For the construction of the expression plasmid DNAs containing CpG sequences in the backbone ((1) and (3) mentioned above), the expression vector pcDNA3.1 purchased from Invitrogen was used. Further, for the construction of the expression plasmid DNAs comprising a backbone not containing any CpG sequence ((2) and (4) mentioned above), the expression vector pCpGfree-mcs purchased from Invitrogen was used.

As for the plasmid DNA (1), the DNA fragment containing the luciferase sequence including CpG sequences was obtained by digesting pGL3-basic vector of Promega with the restriction enzymes HindIII and XbaI. This fragment was introduced into the pcDNA3.1 vector at the HindIII/XbaI sites (pcDNA3.1-Luc(+)).

Figure 6:
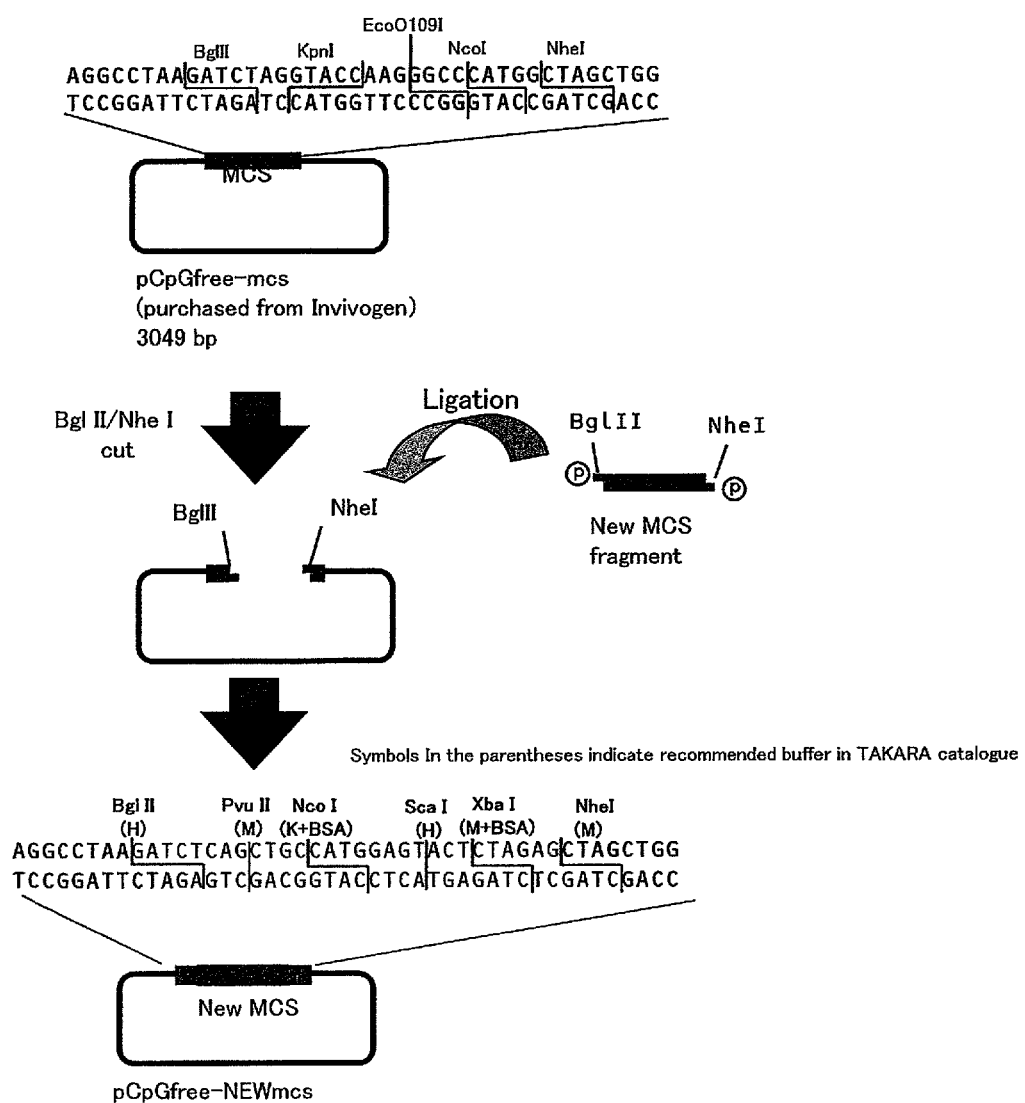
[FIG. 6] This figure depicts a process of constructing a CpG-free plasmid DNA having a new multiple cloning site as the first step of the method for constructing the plasmid DNA (2) described in Example 6.
Figure 7:
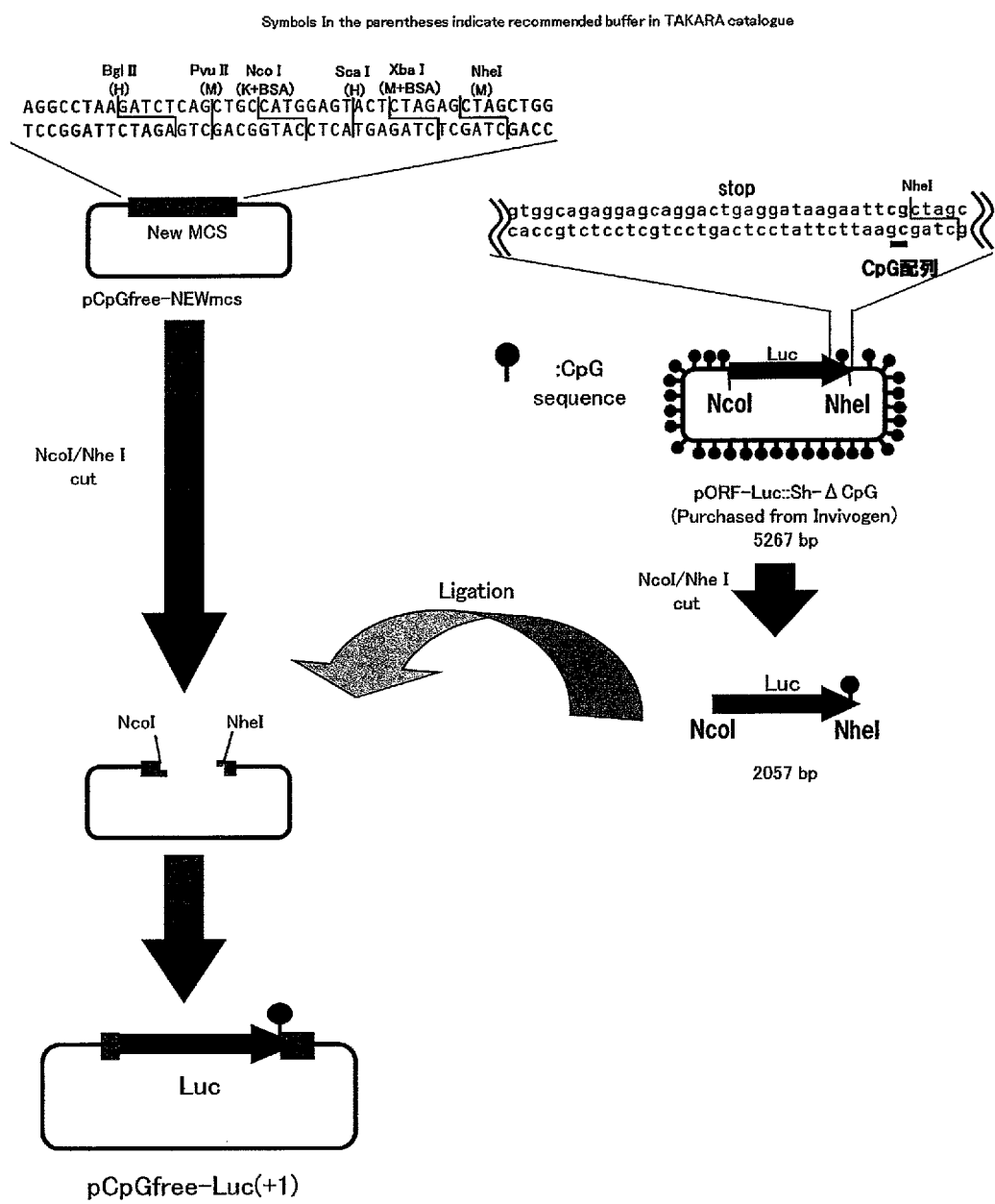
[FIG. 7] This figure depicts a process of incorporating the luciferase gene into CpG-free NEWmcs as the second step of the method for constructing the plasmid DNA (2) described in Example 6.
Figure 8:
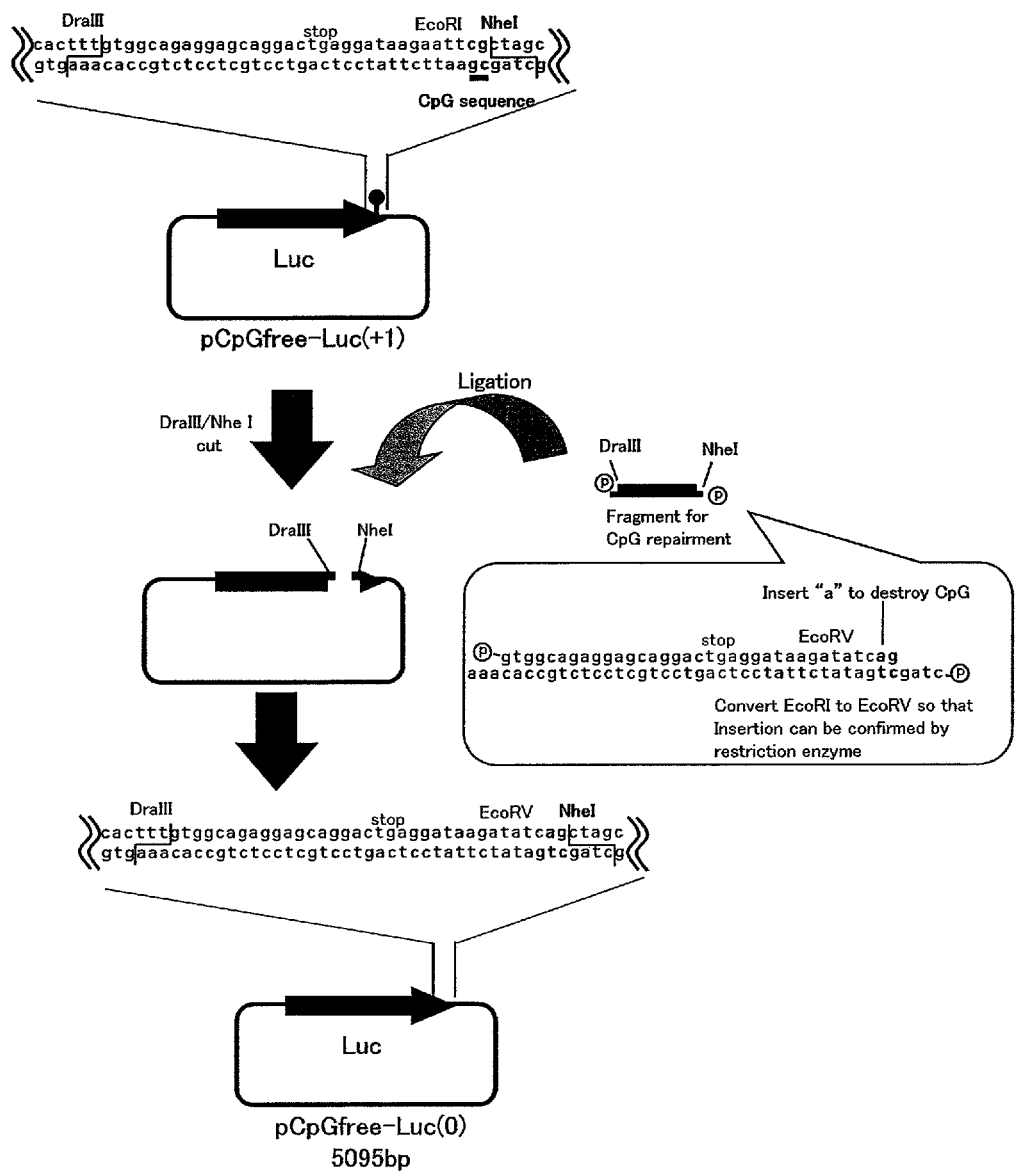
[FIG. 8] This figure depicts a process of removing the remained one CpG sequence as the third step of the method for constructing the plasmid DNA (2) described in Example 6.

As for the plasmid DNA (2), the multi-cloning site of pCpGfree-mcs KpnI-EcoO109I-NcoI-NheI) was treated with BglII/NheI, and a double-stranded DNA fragment having ends complementary to the cleavage sites of these restriction enzymes was inserted to create a new multi-cloning site (BglII-PvuII-NcoI-XbaI-NheI) (pCpGfree-NEWmcs, FIG. 6). A gene encoding luciferase not having CpG sequence obtained by treating pORF-Luc:Sh-ACpG (Invivogen) with NcoI/NheI was introduced into pCpGfree-NEWmcs at the NcoI/NheI sites (pCpGfree-Luc(+1)). The plasmid DNA prepared by this method had only one CpG sequence after the 12th codon counted from the codons of the luciferase gene (FIG. 7). The residual CpG sequence was eliminated by excising a portion of sequence containing the stop codon and the CpG sequence from pCpGfree-Luc(+1) by a DraIII/NheI treatment, and inserting an oligonucleotide having ends complementary to the above restriction enzyme digestion sites, and including a mutation at the site of the CpG sequence. For this operation, the EcoRI site existing immediately downstream of the stop codon was replaced with the EcoRV site (pCpGfree-Luc(0), FIG. 8).

The plasmid DNA (3) was prepared by inserting the CpG-free luciferase gene excised from pCpGfree-Luc(0) prepared in the construction of the plasmid DNA (2) by BglII/EcoRV digestion into pcDNA3.1 at the BamHI/RV site (pcDNA3.1-Luc(0)).

The plasmid DNA (4) was prepared by inserting the luciferase coding gene obtained from pcDNA3.1-Luc(+) prepared in the construction of the plasmid DNA (1) by PmeI/XbaI treatment into pCpGfree-NEWmcs at the PvuII/XbaI digestion site (pCpGfree-Luc(+)).

(b) Isolation and Induction of Mouse Bone Marrow-Derived Dendritic Cells (BMDC)

The thighbones and the neck bones were extracted from C57BL/6 mice (6 to 8 weeks old) sacrificed by cervical vertebra dislocation, mildly disinfected with 70% ethanol, and then immersed into PBS. Both ends of the bones were cut, and the bone marrow cells were pushed out into the RPMI 1640 medium by using a 1-mL syringe containing the medium (26 G needle). The cell suspension was passed through a 40-μm cell strainer (FALCON), and transferred to a 50-mL conical tube. The cell suspension was centrifuged (450 g, 4° C., 5 minutes), then the supernatant was removed, and the cells were dispersed by tapping. Then, the cells were added with ACK Lysing Buffer (1 mL), and they were mixed and left standing at room temperature for 3 to 5 minutes. The cell suspension was added with the medium (10 mL), the mixture was centrifuged, the supernatant was removed, and the cells were further washed twice with the medium (10 mL). Then, the cells were suspended in the medium (10 mL), added to a 10-cm cell culture dish (FALCON), and cultured under the conditions of 37° C. and 5% $CO_2$ for 4 hours or more. Only the floating cells were collected into a 50-mL conical tube by gentle pipetting, and centrifuged, the supernatant was removed, and then the cells were suspended in the medium (10 mL), and counted. The cells were suspended in the medium at a density of $1×10^6$ cells/mL, and added with GM-CSF (final concentration: 10 ng/mL), the cell suspension was dispensed on a 24-well plate (Corning, N.Y.) in a volume of 1 mL/well, and the culture was performed under the conditions of 37° C. and 5% $CO_2$ for two days. After two days and four days, floating cells were removed to leave aggregates of the cells, and the culture was added with a fresh GM-CSF-containing RPMI 1640 medium (1 mL). Floating and weakly adhered cells on the day 6 to 8 from the start of the culture in the presence of GM-CSF were used for the experiment as immature dendritic cells. The purity was 85 to 90% as determined by evaluation using the CD11c antibody (PE Anti-mouse CD 11c, Clone: N418, BioLegend).

(c) Preparation of KALA(SEQ ID NO: 1)-MEND

Each of the various plasmid DNAs obtained in the section (a) mentioned above was dissolved in a 10 mM HEPES buffer at a concentration of 0.1 mg/mL. A 0.1 mg/mL protamine solution (150 μL, 10 mM HEPES buffer) was dropped portionwise with the pDNA solution (100 μL) to prepare a compaction body of protamine and the pDNA (N/P ratio was 2.2).

A 1 mM solution of DOPE (112.5 μL) and a 1 mM solution of CHEMS (25 μL) were put into a glass test tube so as to obtain a DOPE:CHEMS ratio of 9:2. The mixture was added with a 1 mg/mL solution of stearylated KALA (SEQ ID NO: 1) (STR-KALA) in a volume for modifying 5% of the total lipids, and further added with chloroform to a total volume of 200 μL, and the mixture was dried under reduced pressure in a desiccator to evaporate the solvent and thereby obtain a lipid membrane. This lipid membrane was added with the compaction body so that the total lipid concentration became 0.55 mM, and the mixture was left standing at room temperature for 10 minutes to allow hydration, and ultrasonicated for 1 minute with a sonicator. The mixture was further added with stearylated KALA (SEQ ID NO: 1) (STR-KALA, 1mg/mL aqueous solution) in such a volume that the added STR-KALA (SEQ ID NO: 1) amount corresponded to 5 mol % of the total lipids, and the mixture was left standing at room temperature for 10 minutes.

For the preparation of R8 (SEQ ID NO: 4)-MEND, a 1mM solution of DOPE (112.5 μL) and a 1 mM solution of CHEMS (25 µL) were put into a glass test tube so as to obtain a DOPE:CHEMS ratio of 9:2, the mixture was further added with chloroform to a total volume of 200 µL, and the mixture was dried under reduced pressure in a desiccator to evaporate the solvent and thereby obtain a lipid membrane. This lipid membrane was added with the compaction body so that the total lipid concentration became 0.55 mM, and the mixture was left standing at room temperature for 10 minutes to allow hydration, and then ultrasonicated for 1 minute with a sonicator. The mixture was added with stearylated R8 (SEQ ID NO: 4) (STR-R8 , 2 mg/mL aqueous solution) in such a volume that the added STR-R8 (SEQ ID NO: 4) amount corresponded to 5 mol % of the total lipids, and the mixture was left standing at room temperature for 10 minutes.

(d) Evaluation of Gene Expression Activity in BMDC

BMDCs induced by the method described in the section (b) mentioned above were inoculated on a 24-well plate at a density of $4\times10^5$ cells/well. The prepared MEND was diluted with RPMI 1640 (serum-free, antibiotic-free) so that pDNA was to be contained in an amount of 0.4 µg/well, and the volume was adjusted to 500 µL. The MEND solution was applied to each well, and incubation was performed under an environment of 37° C. and 5% $CO_2$. After 3 hours, RPMI 1640 (containing serum and antibiotic, 500 µL) was added to each well, and the luciferase activity was measured further 21 hours afterward. For the measurement of the luciferase activity, the floating cells were collected together with the medium, and centrifuged (4° C., 500 g, 5 minutes), and the supernatant was removed to collect only the cells. The cells remained in each well and the floating cells collected above were added with Reporter Lysis Buffer (1×), and the both were mixed, adjusted to a total volume of 75 µL subjected to pipetting, and frozen at $-80°$ C. The sample frozen at $-80°$ C. was thawed, and the cells were scraped off with a cell scraper and collected in an Eppendorf tube. A lysate of the collected cells was centrifuged at 15,000 rpm and 4° C. for 2 minutes, and 50 µL of the supernatant was collected. The resulting supernatant was used for the measurement of the luciferase activity (RLU/mL). Further, proteins were quantified by the BCA method (mg/mL), and the luciferase activity per unit amount of protein (RLU/mg protein) was calculated.

Figure 9:
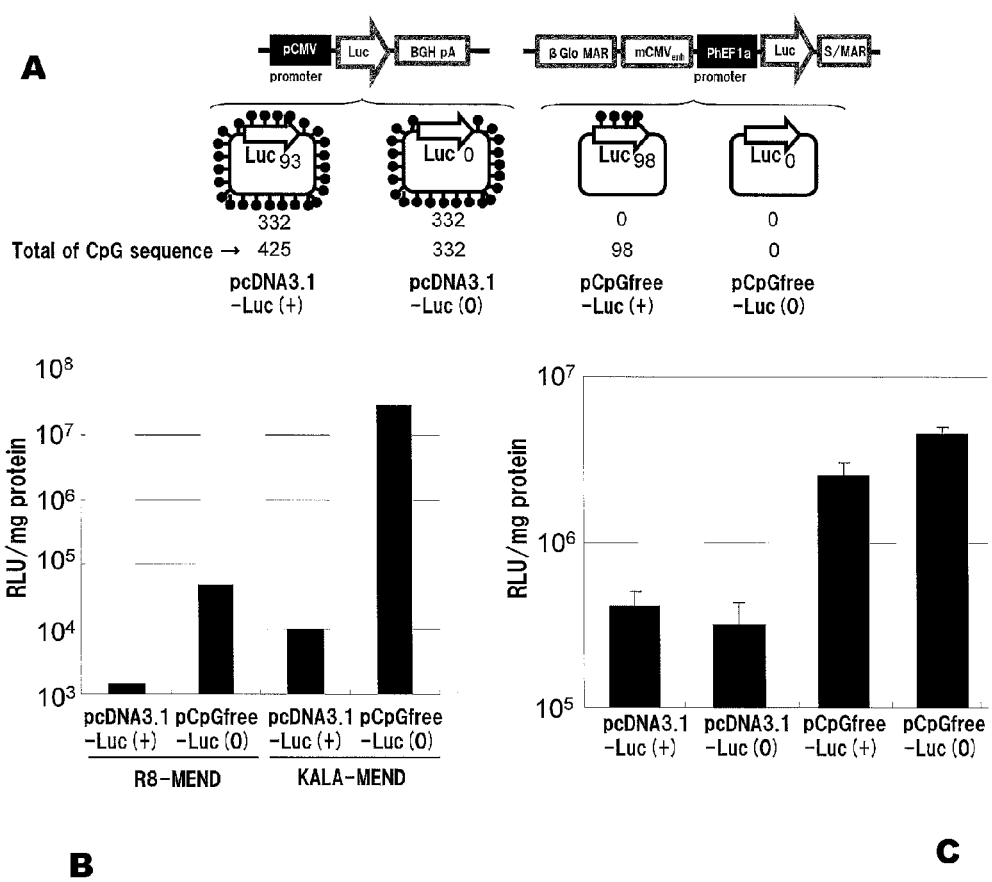
[FIG. 9] This figure depicts the gene expression activity-enhancing effect of KALA (SEQ ID NO: 1)-MEND obtained by modification of vector of introduction plasmid. The top panel (Panel A) shows the pCDNA3.1 and pCpGfree vectors used to determine gene expression activities. The left graph (Panel B) shows the gene expression activities obtained in BMDCs with R8(SEQ ID NO: 4)-MEND and KALA(SEQ ID NO: 1)-MEND using pcDNA3.1-Luc(+) and pCpGfree-Luc(0) prepared in the section (a). The right graph (Panel C) shows the gene expression activities obtained using pcDNA3.1-Luc(+), pcDNA3.1-Luc(0), pCpGfree-Luc(+), and pCpGfree-Luc(0).

The results are shown in FIG. 9. The left graph shows the gene expression activities obtained in BMDCs with R8(SEQ ID NO: 4)-MEND and KALA(SEQ ID NO: 4)-MEND using (1) pcDNA3.1-Luc(+) and (4) pCpGfree-Luc(0) prepared in the section (a). When pCpGfree-Luc(0) was used, high gene expression activity-promoting effect was observed with both R8(SEQ ID NO: 4)-MEND and KALA (SEQ ID NO: 1)-MEND. In particular, it was revealed that when (2) pCpG-free-Luc(0) was enclosed in KALA (SEQ ID NO: 1)-MEND, there could be attained a gene expression level enabling antigen presentation expectable on the basis of the results of Examples 2 and 3 performed by using JAWS II (about $10^7$ RUL/mg protein).

When the CpG sequence was eliminated only from the insert ((3) pcDNA3.1-Luc(0)), increase of the gene expression was not observed. Whist, when the CpG sequence was eliminated from the backbone ((4) pCpGfree-Luc(+)), promotion of the gene expression activity was observed. From these results, it was demonstrated that, as for selection of promoter, a combination of the mouse CMV enhancer and the human elongation factor 1 alpha core promoter was useful for gene transfer into dendritic cell. Further, (2) pCpGfree-Luc (0) in which the CpG sequence was completely eliminated gave higher gene expression compared with (3) pCpGfree-Luc(+), and accordingly, it was demonstrated that a plasmid DNA having the mouse CMV enhancer and the human elongation factor 1 alpha core promoter, from which the CpG sequence was completely eliminated, was most suitable for dendritic cells.

Example 7

Vaccine Effect for Prophylaxis of Cancer (a) Preparation of CpG-free OVA Expression Plasmid DNA An antigen (OVA) gene sequence containing no CpG sequence was designed (DNA sequence of 1161 bp shown in SEQ ID NO: 2 of Sequence Listing), and custom-made synthesis thereof was entrusted (TAKARA). This sequence was subcloned into pCpGfree-NEWmcs at one of the multi-cloning sites thereof, the NcoI/NheI site (pCpGfree-OVA(0)).

(b) Gene Transfer of Antigen (OVA) Expression Plasmid DNA into BMDC and Stimulation with Adjuvant The dendritic cells isolated and differentiated by the method described in Example 6, (b) were inoculated on a 24-well plate at a density of $4\times10^5$ cells/well. KALA-MEND was prepared by using the CpG-free OVA expression plasmid DNA (pCpGfree-OVA(0)) according to the method described in Example 6, (c). MEND was diluted with RPMI 1640 (serum-free, antibiotic-free) so that pDNA was to be contained in an amount of 0.4 µg/well, and the volume was adjusted to 500 µL. The MEND solution was applied to each well, and the mixture was incubated under an environment of 37° C. and 5% 002. After 3 hours, RPMI 1640 (containing serum and antibiotic, 500 µL) was added to each well, and the cells were collected further 21 hours afterward. The floating cells and the adhered cells exfoliated by pipetting in PBS were combined, and collected by centrifugation (4° C., 500 g, 5 minutes).

When BMDCs were activated by using CpG oligonucleotide as an adjuvant, incubation was conducted at a concentration of 1 µg/mL with BMDCs for 1 hour in RPMI 1640 (serum-free, antibiotic-free) before the transfection of KALA-MEND.

(c) Evaluation of Antitumor Effect

Fourteen days and seven days before transplantation of antigen (OVA)-expressing tumor cells (E.G7-OVA cells), (1) BMDCs on which only CpG as an adjuvant of DC was acted, (2) BMDCs in which luciferase as a non-antigen protein was expressed by using KALA-MEND, (3) BMDCs in which the antigen protein (OVA) was expressed by using KALA-MEND, and (4) BMDCs in which the antigen protein (OVA) was expressed by using KALA-MEND, and which were activated with CpG adjuvant were prepared at a density of $4\times10^5$ cells/40 µL in PBS, and the total volume of each was administered to C57BL/6 mice (female, 8 weeks old) at the planta pedis. One week after the second immunization, $8\times10^5$ of the E.G7-OVA cells were transplanted to the mice at the left flank, and the tumor volume was periodically measured. The tumor volume ($mm^3$) was calculated in accordance with the equation: tumor volume=major axis×minor axis×minor axis× 0.52.

Figure 10:
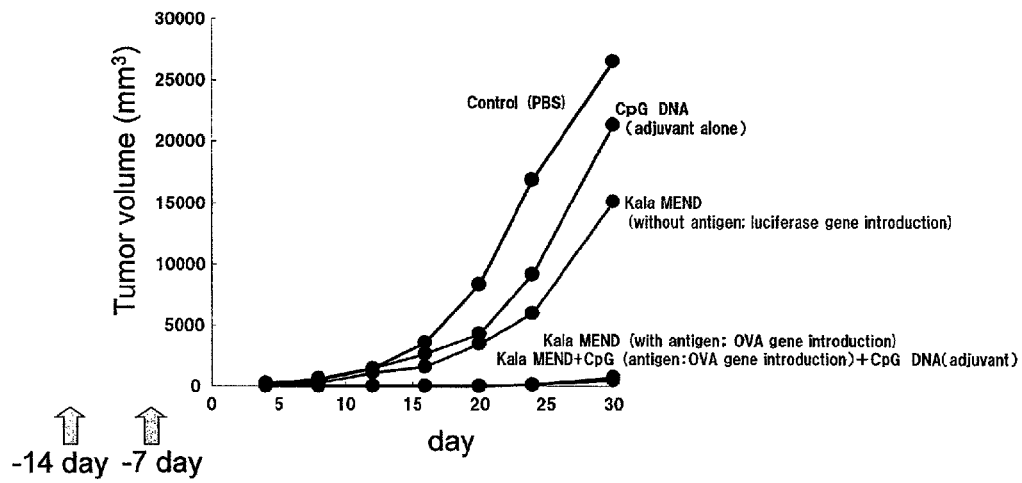
[FIG. 10] This figure depicts the result that MEND of which surface was modified with KALA (SEQ ID NO: 1) showed high antitumor activity irrespective of the presence or absence of adjuvant.
Figure 11:
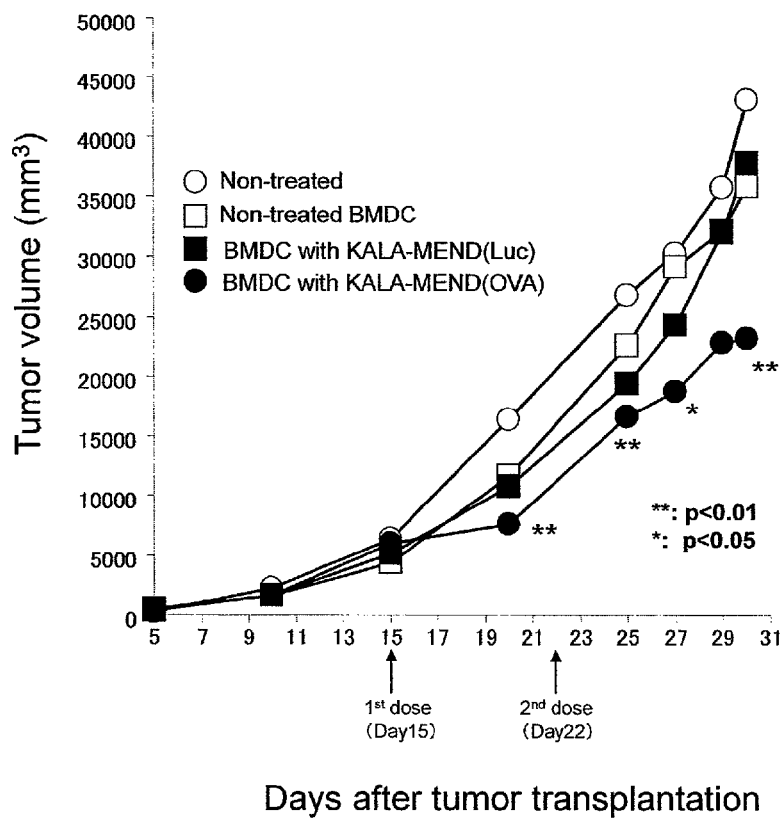
[FIG. 11] This figure depicts antitumor effect obtained by administering MEND of which surface was modified with KALA after the tumor was formed.

The results are shown in FIG. 10. Decrease of tumor growth was observed after applying the adjuvant stimulation with the CpG sequence compared with the control group administered with PBS, and it was revealed that this effect was obtained at a higher degree with KALA-MEND (non-antigen protein, expressing luciferase). This result supports the results of Examples 4 and 5 showing that KALA-MEND itself had a high adjuvant effect. Further, when the OVA expression plasmid DNA was introduced by using KALA-MEND, almost comparable extremely high tumor preventing effects were observed with or without CpG as an adjuvant.

From these results, it was revealed that KALA-MEND successfully imparted an antigen expression level sufficient for exhibiting cytotoxicity activity to BMDCs, and also had an adjuvant effect.

Example 8

Tumor Growth-Suppressing Effect (a) Gene Transfer of Antigen (OVA) Expression Plasmid DNA into BMDC Dendritic cells isolated and differentiated by the method described in Example 6, (b) were inoculated on a 24-well plate at a density of $4\times10^5$ cells/well. KALA-MEND was prepared by using the CpG-free OVA expression plasmid DNA (pCpGfree-OVA(0)) according to the method described in Example 6, (c). MEND was diluted with RPMI 1640 (serum-free, antibiotic-free) so that pDNA was to be contained in an amount of 0.8 μg/well, and the volume was adjusted to 500 μL. The MEND solution was applied to each well, and incubation was performed under an environment of 37° C. and 5% $CO_2$. After 3 hours, RPMI 1640 (containing serum and antibiotic, 500 μL) was added to each well, and the cells were collected further 21 hours afterward. The floating cells and the adhered cells exfoliated by pipetting in PBS were combined, and collected by centrifugation (4° C., 500 g, 5 minutes).

(b) Evaluation of Antitumor Effect

The antigen (OVA)-expressing tumor cells (E.G7-OVA cells, $8\times10^5$ cells) were transplanted to C57BL/6 mice (female, 8-weeks old) at the left flank, and on the day 15 and the day 22 after the transplantation, (1) untreated BMDCs, (2) BMDCs in which luciferase as a non-antigen protein was expressed by using KALA-MEND, and (3) BMDCs in which the antigen protein (OVA) was expressed by using KALA-MEND were each suspended in 40 μL of PBS so that $4\times10^5$ BMDCs were contained, and administered to the mice at the planta pedis. The tumor size was periodically measured, and tumor volume ($mm^3$) was calculated in accordance with the equation: tumor volume=major axis×minor axis×minor axis× 0.52.

Although antitumor effect was not observed with untreated DCs and the non-antigen protein-expressing BMDCs, superior anti-tumor proliferation effect was observed with OVA-expressing KALA-MEND compared with the untreated mice. Therefore, it was revealed that even if KALA-MEND was administered after a tumor was formed, it successfully provided an antitumor effect.

Industrial Applicability

The lipid membrane structure provided by the present invention can efficiently migrate into nuclei of any types of cells such as immunocytes including dendritic cells, efficiently release an encapsulated substance such as nucleic acid in the nuclei to allow expression of a polypeptide encoded by such a nucleic acid, and further exhibit an efficient adjuvant effect. Therefore, the lipid membrane structure has a characteristic feature that it enables effective immunotherapy against an arbitrary polypeptide for which immunotherapy is desired.

What is claimed is:

1. A lipid membrane structure for delivering a substance into a nucleus of a cell that encapsulates the substance to be delivered and that is modified with a polypeptide having amino acid residues which consist of the amino acid residues in the amino acid sequence of SEQ ID NO: 1.

2. The lipid membrane structure according to claim 1, wherein the lipid membrane structure is a liposome.

3. The lipid membrane structure according to claim 1, wherein the polypeptide is modified with a hydrophobic group, and the hydrophobic group is inserted into the lipid membrane.

4. The lipid membrane structure according to claim 1, which has a polypeptide containing a plurality of contiguous arginine residues on the surface.

5. The lipid membrane structure according to claim 1, which has a polyalkylene glycol on the surface.

6. The lipid membrane structure according to claim 1, wherein a nucleic acid and a cationic polymer are enclosed in the inside of the lipid membrane structure.

7. The lipid membrane structure according to claim 1, wherein the substance to be delivered is a nucleic acid encoding an antigen polypeptide to be presented on the surface of an immunocyte.

8. The lipid membrane structure according to claim 7, wherein the nucleic acid is DNA, and the DNA does not contain CpG.

9. A pharmaceutical composition containing the lipid membrane structure according to claim 1 as an active ingredient.

10. A polypeptide having amino acid residues which consist of the amino acid residues in the amino acid sequence of SEQ ID NO: 1.

* * * * *

SEQUENCE LISTING

```
<160> NUMBER OF SEQ ID NOS: 13

<210> SEQ ID NO 1
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala
            20                  25

<210> SEQ ID NO 2
<211> LENGTH: 1161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgggctcaa ttggtgcagc atcaatggag ttctgctttg atgttttcaa ggagctgaaa      60
gtgcaccatg caaatgagaa tattttttac tgcccaatag caataatgtc agcccttgct     120
atggtgtatc tgggggccaa ggactccacc agaacccaaa tcaacaaggt tgtaaggttt     180
gacaagctgc caggctttgg tgactcaata gaggcccagt gtggcaccag tgtaaatgta     240
cactcctccc taagggatat actgaaccag ataaccaagc caatgatgt gtacagcttc      300 tccttggcaa gcagactata tgcagaggag aggtacccaa tcttgcctga atacctgcag     360
```

```
tgtgtcaagg aactttacag aggggggccta gagcccatca actttcagac tgcagctgac    420
caagcaaggg agttaatcaa ctcttgggtg gagagccaga ccaatggaat aatcaggaat    480
gttctgcagc cttcatctgt agactcccag acagcaatgg tcttggtcaa tgcaattgtc    540
ttcaagggcc tgtgggagaa gactttcaaa gatgaagaca ctcaggcaat gcccttcaga    600
gtaactgaac aggagtccaa acctgtgcag atgatgtacc aaattgggtt attcagggtg    660
gcttcaatgg cttctgagaa aatgaagatt ctggagttac cctttgccag tgggacaatg    720
tctatgctgg tcctgttacc agatgaggtg tcagggcttg agcagctgga gtcaatcatc    780
aattttgaga agtaacaga gtggacctcc tccaatgtca tggaagaaag gaaaatcaag    840
gtctacctgc ccagaatgaa aatggaggag aaatacaacc tcacctcagt gttgatggca    900
atggggataa cagatgtctt ctccagctct gccaacctct ctggcatcag cagtgctgaa    960
tccctaaaga tatcacaggc tgttcatgca gcccatgcag aaatcaatga agcaggcagg   1020
gaggtggtgg gctctgctga ggcaggagtg gatgctgcct ctgtctcaga agagttcaga   1080
gcagaccacc ccttcctctt ctgcatcaag catatagcca ccaatgctgt tcttttcttt   1140
ggaaggtgtg tgtcccccta a                                             1161
```

```
<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This sequence may encompass 4-20 residues

<400> SEQUENCE: 3

Arg Arg Arg Arg Arg Arg Arg Arg Arg Arg Arg Arg Arg Arg Arg
1               5                   10                  15

Arg Arg Arg Arg
            20

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Arg Arg Arg Arg Arg Arg
1               5

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
```

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
aggcctaaga tctaggtacc aagggcccat ggctagctgg          40

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
aggcctaaga tctcagctgc catggagtac tctagagcta gctgg    45

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
gtggcagagg agcaggactg aggataagaa ttcgctagc           39

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
cactttgtgg cagaggagca ggactgagga taagaattcg ctagc    45

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
gtggcagagg agcaggactg aggataagat atcag               35

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
ctagctgata tcttatcctc agtcctgctc ctctgccaca aa       42

-continued

```
<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cactttgtgg cagaggagca ggactgagga taagatatca gctagc                  46

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30
```